(12) United States Patent
Díaz-Fernández et al.

(10) Patent No.: US 9,676,784 B2
(45) Date of Patent: Jun. 13, 2017

(54) FUSED IMIDAZOLYL DERIVATIVES, THEIR PREPARATION AND USE AS MEDICAMENTS

(71) Applicant: LABORATORIOS DEL DR. ESTEVE S.A., Barcelona (ES)

(72) Inventors: José-Luis Díaz-Fernández, Manresa (ES); Carmen Almansa-Rosales, Barcelona (EP); Piotr Nieczypor, Nijmegen (NL)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 15/105,105

(22) PCT Filed: Dec. 18, 2014

(86) PCT No.: PCT/EP2014/078457
§ 371 (c)(1),
(2) Date: Jun. 16, 2016

(87) PCT Pub. No.: WO2015/091795
PCT Pub. Date: Jun. 25, 2015

(65) Prior Publication Data
US 2016/0311828 A1    Oct. 27, 2016

(30) Foreign Application Priority Data
Dec. 20, 2013   (EP) .................................... 13384003

(51) Int. Cl.
*C07D 487/04*    (2006.01)

(52) U.S. Cl.
CPC .................................. *C07D 487/04* (2013.01)

(58) Field of Classification Search
CPC .................................................... C07D 487/04
See application file for complete search history.

(56) References Cited

U.S. PATENT DOCUMENTS

| | | |
|---|---|---|
| 2007/0232585 A1 | 10/2007 | Corbera Arjona et al. |
| 2009/0209568 A1 | 8/2009 | Wünsch |
| 2010/0184759 A1 | 7/2010 | Wünsch et al. |
| 2010/0197714 A1 | 8/2010 | Wünsch et al. |

FOREIGN PATENT DOCUMENTS

| | | |
|---|---|---|
| EP | 2548878 | 1/2013 |
| WO | WO 02/053558 | 7/2002 |
| WO | WO 03/076427 | 9/2003 |
| WO | WO 2012/072791 | 6/2012 |

OTHER PUBLICATIONS

Collina, et al., Expert Opin. Ther. Patents, 2013, 23, 597-613.
International Search Report for International Application No. PCT/EP2014/078457 dated Apr. 8, 2015.

*Primary Examiner* — Kahsay Habte
(74) *Attorney, Agent, or Firm* — Hueschen and Sage

(57) ABSTRACT

The present invention relates to new fused imidazolyl derivatives having a high affinity for sigma receptors, especially sigma-1 receptors, as well as to the process for the preparation thereof, to compositions comprising them, and to their use as medicaments.

15 Claims, No Drawings

FUSED IMIDAZOLYL DERIVATIVES, THEIR PREPARATION AND USE AS MEDICAMENTS

FIELD OF THE INVENTION

The present invention relates to new fused imidazolyl derivatives having a high affinity for sigma receptors, especially sigma-1 receptors, as well as to the process for the preparation thereof, to compositions comprising them, and to their use as medicaments.

BACKGROUND OF THE INVENTION

The search for new therapeutic agents has been improved in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF-10047, (+)-cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by different drugs. (+)-SKF-10047 has nanomolar affinity for the sigma 1 ($\sigma_1$) site, and micromolar affinity for the sigma 2 ($\sigma_2$) site. Haloperidol has similar affinities for both subtypes.

The $\sigma_1$ receptor is a chaperone protein expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for (+)-SKF-10047, (+)-pentazocine, haloperidol and rimcazole, among others, known ligands with analgesic, anxiolytic, antidepressive, antiamnesic, antipsychotic and neuroprotective activity. The $\sigma_1$ receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The $\sigma_2$ receptor is also expressed in numerous adult mammal tissues (e.g. nervous system, immune system, endocrine system, liver, kidney). $\sigma_2$ receptors can be components in a new apoptosis route that may play an important role in regulating cell proliferation or in cell development. This route seems to consist of $\sigma_2$ receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of $\sigma_2$ receptors induce changes in cell morphology, apoptosis in several types of cell lines and regulate the expression of p-glycoprotein mRNA, so that they are potentially useful as antineoplasic agents for treatment of cancer. In fact, $\sigma_2$ receptor agonists have been observed to induce apoptosis in mammary tumour cell lines resistant to common antineoplasic agents that damage DNA. In addition, agonists of $\sigma_2$ receptors enhance the cytotoxic effects of these antineoplasic agents at concentrations in which the agonist is not cytotoxic. Thus, agonists of $\sigma_2$ receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of $\sigma_2$ receptors can prevent the irreversible motor side effects caused by typical neuroleptic agents. In fact, it has been found that antagonists of $\sigma_2$ receptors can be useful as agents for improving the weakening effects of delayed dyskinesia appearing in patients due to chronic treatment of psychosis with typical antipsychotic drugs, such as haloperidol. $\sigma_2$ receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of σ receptors in the CNS, immune and endocrine systems have suggested a likelihood that it may serve as link between the three systems.

In view of the potential therapeutic applications of agonists or antagonists of the a receptor, a great effort has been directed to find selective ligands. Different a receptor ligands have been reported.

For instance, the international patent application WO-2008/055932 deals with 1,2,4-triazole compounds having good activity towards a receptors. WO-2009/071657 also reports tricyclic triazolic compounds having good activity towards a receptors. Pyrazoles compounds have been described in the international application WO-2011/147910 as σreceptor inhibitors.

Some fused compounds have also been reported as a ligands. For instance the pyrazolo[3,4-d]pyrimidine disclosed in the international application WO-2013/010950, as well as the pyrazolo[1,5-a]pyridines described in WO-2013/124341.

Nevertheless, there is still a need to find compounds having pharmacological activity towards the σreceptor, being both effective and selective, and having good "drugability" properties, i.e. good pharmaceutical properties related to administration, distribution, metabolism and excretion.

SUMMARY OF THE INVENTION

The present invention discloses novel compounds with high affinity to sigma receptors which might be used for the treatment of sigma related disorders or diseases.

In a main aspect, the present invention is directed to novel fused imidazolyl derivatives of general formula (I):

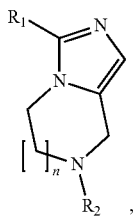

where $R_1$, $R_2$ and n are as defined below.

Another object of the invention relates to the different processes for preparation of compounds of general formula (I).

Another object of the invention refers to the use of such compounds of general formula (I) for the treatment or prophylaxis of σ receptor mediated diseases or conditions, especially $\sigma_1$ mediated diseases or conditions. Within the group of diseases or conditions mediated by the σ receptor for which the compounds of the invention are effective, diarrhea, lipoprotein disorders, hyperlipidemia, hypertriglyceridemia, hypercholesterolemia, obesity, migraine, pain, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, may be cited. Compounds of the invention are very good and are especially effective for the treatment and prophylaxis of pain, especially neuropathic pain, inflammatory pain or other pain conditions involving allodynia and/or hyperalgesia.

It is also an object of the invention to provide pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to a compound of general formula (I):

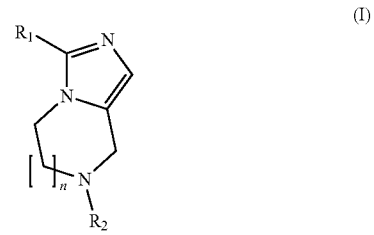

where $R_1$ is selected from the group consisting of $-NR_4COR_3$, $-NHCONHR_3$, $-(C(R_{51}R_{52}))_m-R_6$, and $-NR_{71}R_{72}$;

$R_2$ is selected from the group consisting of $-(C(R_{81}R_{82}))_p-R_9$, a substituted or unsubstituted cycloalkyl group, a substituted or unsubstituted heterocycloalkyl group;

$R_3$ is selected from the group consisting of a linear or branched, substituted or unsubstituted $C_{1-10}$ aliphatic radical, a substituted or unsubstituted cycloalkyl group, a substituted or unsubstituted cycloalkylalkyl group, a substituted or unsubstituted heterocycloalkyl group, a substituted or unsubstituted heterocycloalkylalkyl group;

$R_4$, is selected from the group consisting of a hydrogen atom, a linear or branched, substituted or unsubstituted $C_{1-10}$ aliphatic radical, a substituted or unsubstituted cycloalkyl group, a substituted or unsubstituted cycloalkylalkyl group, a substituted or unsubstituted aryl group, a substituted or unsubstituted arylalkyl group, a substituted or unsubstituted heterocycloalkyl group, a substituted or unsubstituted heterocycloalkylalkyl group, a substituted or unsubstituted heteroaryl group, a substituted or unsubstituted heteroarylalkyl group;

$R_{51}$, $R_{52}$, $R_{81}$ and $R_{82}$ are selected independently from the group consisting of a hydrogen atom, a linear or branched, substituted or unsubstituted $C_{1-3}$ aliphatic radical;

$R_6$ is selected from the group consisting of a substituted or unsubstituted aryl group, a substituted or unsubstituted heteroaryl group;

$R_{71}$ is selected from the group consisting of a substituted or unsubstituted cycloalkyl group, a substituted or unsubstituted cycloalkylalkyl group, a substituted or unsubstituted aryl group, a substituted or unsubstituted arylalkyl group, a substituted or unsubstituted heterocycloalkyl group, a substituted or unsubstituted heterocycloalkylalkyl group, a substituted or unsubstituted heteroaryl group, a substituted or unsubstituted heteroarylalkyl group;

$R_{72}$ is selected from the group consisting of a hydrogen atom, a linear or branched, substituted or unsubstituted $C_{1-3}$ aliphatic radical;

$R_9$ is selected from the group consisting of a substituted or unsubstituted cycloalkyl group, a substituted or unsubstituted aryl group, a substituted or unsubstituted heterocycloalkyl group, a substituted or unsubstituted heteroaryl group;

n is 1, 2, or 3;
m is 1, 2, or 3;
p is 1, 2, or 3;

as well as one of the stereoisomers, preferably enantiomers or diastereomers, a racemate or as a mixture of at least two of the stereoisomers, preferably enantiomers and/or diastereomers, in any mixing ratio, or a pharmaceutically acceptable salt or solvate thereof.

"Halogen" or "halo" as referred in the present invention represent fluorine, chlorine, bromine or iodine.

Aliphatic radical $C_{1-10}$, as referred to in the present invention, are optionally mono- or polysubstituted and may be branched or unbranched, saturated or unsaturated. Unsaturated aliphatic radicals, as defined in the present invention, include alkenyl and alkynyl radicals. Preferred aliphatic radicals according to the present invention include but are not restricted to methyl, ethyl, vinyl (ethenyl), ethynyl, propyl, n-propyl, isopropyl, allyl (2-propenyl), 1-propynyl, methylethyl, butyl, n-butyl, iso-butyl, sec-butyl, tert-butyl butenyl, butynyl, 1-methylpropyl, 2-methylpropyl, 1,1-dimethylethyl, pentyl, n-pentyl, isopentyl, 1,1-dimethylpropyl, 1,2-dimethylpropyl, 2,2-dimethylpropyl, hexyl, 1-methylpentyl, n-heptyl, n-octyl, n-nonyl and n-decyl. Aliphatic radicals as defined in the present invention are optionally mono- or polysubstituted by one or more substituents independently selected from a $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —Sо$_2$R', —NHR', —NR'R" whereby R' and optionally R" for each substituent independently represents a linear or branched $C_{1-6}$-alkyl radical.

Preferred aliphatic radicals $C_{1-10}$ according to the invention are alkyl radicals $C_{1-10}$.

Alkyl radicals $C_{1-10}$, as referred to in the present invention, are saturated aliphatic radicals $C_{1-10}$. They may be linear or branched and substituted or unsubstituted. Among the alkyl radicals $C_{1-10}$, the alkyl radicals $C_{1-6}$ are preferred. The $C_{1-6}$ alkyl radicals as expressed in the present invention means an alkyl radical of 1, 2, 3, 4, 5 or 6 carbon atoms. In a more preferred aspect of the invention, the alkyl radicals are unsubstituted.

Cycloalkyl group $C_{3-9}$, as referred to in the present invention, are understood as meaning saturated and unsaturated (but not aromatic), cyclic hydrocarbons, which can optionally be unsubstituted, mono- or polysubstituted. In particular the cycloalkyl groups according to the invention are saturated $C_{3-9}$ cycloalkyl group. In these radicals, for example $C_{3-4}$-cycloalkyl represents $C_3$- or $C_4$-cycloalkyl, $C_{3-6}$-cycloalkyl represents $C_3$-, $C_4$- or $C_5$-cycloalkyl, etc. Cycloalkyl group also include mono- or polyunsaturated, preferably monounsaturated, but not aromatic cycloalkyl groups. Examples for cycloalkyl group preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, adamantyl, noradamantyl, tetralinyl or indanyl. Cycloalkyl group $C_{3-9}$, as defined in the present invention, are optionally mono- or polysubstituted by one or more substituents independently selected from a $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —Sо$_2$R', —NHR', —NR'R" whereby R' and optionally R" for each substituent independently represents a linear or branched $C_{1-6}$-alkyl radical. In a more preferred aspect of the invention, the cycloalkyl group $C_{3-9}$ represents a group chosen from cyclopropyl, cyclopropylmethyl, cyclobutyl, cyclopentyl, cyclopentylmethyl and cyclohexyl, and especially a cyclohexyl group.

A heterocycloalkyl group, as referred to in the present invention, is understood as meaning saturated and unsaturated (but not aromatic), cyclic hydrocarbons in which optionally at least one carbon atom is replaced by a heteroatom, preferably S, N or O. Heterocycloalkyl group also include mono- or polyunsaturated, preferably monounsaturated, but not aromatic heterocycloalkyl groups. Heterocycloalkyl group according to the invention can optionally be unsubstituted, mono- or polysubstituted by one or more substituents independently selected from a $C_{1-6}$ alkyl radical, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —Sо$_2$R', —NHR', —NR'R" whereby R' and optionally R" for each substitutent independently represents a linear or branched $C_{1-6}$-alkyl radical. Examples for heterocycloalkyl group preferably include but are not restricted to pyrrole, pyrroline, pyrrolidine, pyrrolidineone, pyrazoline, pyrazolinone, oxopyrazolinone, aziridine, azetidine, tetrahydropyrrole, oxirane, oxetane, dioxetane, tetrahydropyrane, tetrahydrofurane, tetrahydro-2H-thiopyran, dioxane, dioxolane, oxathiolane, oxazolidine, thiirane, thietane, thiolane, thiane, thiazolidine, pyrazine piperidine, piperazine, morpholine, azepane or diazepane. Advantageously, the heterocycloalkyl group of the compounds according to the invention represents a group chosen from pyrrole, pyrroline, pyrrolidine, pyrazoline, tetrahydropyrrole, tetrahydropyrane, tetrahydrofurane, dioxane, pyrazine piperidine, piperazine and morpholine and especially a morpholine group.

An aryl group, as referred to in the present invention, is understood as meaning aromatic ring systems without heteroatoms even in only one of the rings. These aryl groups may optionally be mono- or polysubstituted by one or more substituents independently selected from a $C_{1-6}$ alkyl radical, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —Sо$_2$R', —NHR', —NR'R" whereby R' and optionally R" for each substitutent independently represents a linear or branched $C_{1-6}$-alkyl radical. Preferred examples of aryl radicals include but are not restricted to phenyl, naphthyl, fluoranthenyl, fluorenyl, or anthracenyl radicals, which may optionally be mono- or polysubstituted, if not defined otherwise. In a more preferred aspect of the invention, the aryl group is a phenyl group.

A heteroaryl group, is understood as meaning aromatic ring system in which at least one carbon atom is replaced by a heteroatom chosen from the group consisting of nitrogen, oxygen and/or sulfur and may optionally be mono- or polysubstituted by one or more substituents independently selected from a $C_{1-6}$ alkyl radical, a linear or branched $C_{1-6}$ alkoxy group, F, Cl, I, Br, CF$_3$, CH$_2$F, CHF$_2$, CN, OH, SH, NH$_2$, oxo, (C═O)R', SR', SOR', SO$_2$R', NHR', NR'R" whereby R' and optionally R" for each substituent independently represents a linear or branched $C_{1-6}$ alkyl radical. Preferred examples of heteroaryls include but are not restricted to furan, benzofuran, thiophene, benzothiophene, pyridine, pyrimidine, pyridazine, pyrazine, quinoline, isoquinoline, phthalazine, benzo-1,2,5-thiadiazole, benzothiazole, triazole, pyrazole, isoxazole, indole, benzotriazole, benzodioxolane, benzodioxane, benzimidazole, carbazole and quinazoline. In a more preferred aspect of the invention, the heteroaryl group is a pyridyl group.

In a particularly preferred embodiment of the present invention, the alkyl radicals $C_{1-10}$, the cycloalklyl group $C_{3-9}$, the heterocycloalkyl group, the aryl group and the heteroaryl group are unsubstituted or substituted by one or more substituents selected from a $C_{1-6}$ alkyl radical, a linear or branched $C_{1-6}$ alkoxy group, F, Cl, I, Br and OH.

The terms "condensed" or "fused" according to the present invention mean that a ring or ring-system is attached to at least another ring or ring-system, whereby the rings or ring systems have at least one bond in common, and whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" or "pharmaceutically acceptable salt" is understood in particular, in the context of this invention, as salt (as defined above) formed either with a physiologically tolerated acid, that is to say salts of the particular active compound with inorganic or organic acids which are physiologically tolerated-especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with $NH_4$.

The term "solvate" is to be understood as meaning any form of the active compound according to the invention in which this compound has attached to it via non-covalent binding another molecule (most likely a polar solvent) especially including hydrates and alcoholates, e.g. methanolate.

An aspect of the invention relates to prodrugs of compounds of formula (I) as defined above.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (april 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular embodiment of the compounds of formula (I) according to the invention $R_1$ represents a group $-NR_{71}R_{72}$.

In particularly preferred embodiment of the compounds of formula (I) according to the invention, $R_1$ represents a group $-NR_{71}R_{72}$ in which $R_{71}$ is a substituted or unsubstituted aryl group and $R_{72}$ is a hydrogen atom.

In another embodiment, the compounds of formula (I) of the present invention are those where $R_1$ represents a group $-(C(R_{51}R_{52}))_m-R_6$ in which $R_6$ is preferably a substituted or unsubstituted aryl group.

In a further particular embodiment of the compounds of formula (I) according to the invention, $R_1$ is selected from the group consisting of $-NR_4COR_3$, and $-NHCONHR_3$.

A further aspect of the present invention is directed particularly to compounds of formula (I) according to the invention where $R_2$ is a $-(C(R_{81}R_{82}))_p-R_9$ group.

A further aspect of the invention is directed to compounds of formula (I) according to the invention where $R_2$ is a $-(C(R_{81}R_{82}))_p-R_3$ group in which $R_{51}$ and $R_{52}$ represent each a hydrogen atom. In a still further particular aspect of the compounds of formula (I) according to the invention the group $R_9$ represents a substituted or unsubstituted cycloalkyl group. In another further particular aspect of the compounds of formula (I) according to the invention the group $R_9$ represents a substituted or unsubstituted aryl group. In another further particular aspect of the compounds of formula (I) according to the invention the group $R_9$ represents a substituted or unsubstituted heterocycloalkyl group. In another further particular aspect of the compounds of formula (I) according to the invention the group $R_9$ represents a substituted or unsubstituted heteroaryl group.

A still further aspect of the invention is directed to compounds of formula (I) according to the invention where, taking together or separately n is 1 or 2, preferably 1, m is 1, p is 1.

In a more preferred variant of the invention, the sigma ligand of formula (I) is selected from:
1-(8-(cyclohexylmethyl)-6,7,8,9-tetrahydro-5H-imidazo[1,5-a][1,4]diazepin-3-yl)-3-ethylurea,
1-(7-(cyclohexylmethyl)-5,6,7,8-tetrahydroimidazo[1,5-a]pyrazin-3-yl)-3-ethylurea,
1-(7-(cyclohexylmethyl)-5,6,7,8-tetrahydroimidazo[1,5-a]pyrazin-3-yl)-3-propylurea,
1-tert-butyl-3-(7-(cyclohexylmethyl)-5,6,7,8-tetrahydroimidazo[1,5-a]pyrazin-3-yl)urea,
7-(cyclohexylmethyl)-N-phenyl-5,6,7,8-tetrahydroimidazo[1,5-a]pyrazin-3-amine,
7-(cyclohexylmethyl)-N-(3,5-difluorophenyl)-5,6,7,8-tetrahydroimidazo[1,5-a]pyrazin-3-amine,
7-(cyclohexylmethyl)-N-(3-methoxyphenyl)-5,6,7,8-tetrahydroimidazo[1,5-a]pyrazin-3-amine,
7-(cyclohexylmethyl)-N-(4-fluorophenyl)-5,6,7,8-tetrahydroimidazo[1,5-a]pyrazin-3-amine,
7-benzyl-N-(3-chloro-2-fluorophenyl)-5,6,7,8-tetrahydroimidazo[1,5-a]pyrazin-3-amine,
7-benzyl-N-phenyl-5,6,7,8-tetrahydroimidazo[1,5-a]pyrazin-3-amine,
N-(3,5-difluorophenyl)-7-((tetrahydro-2H-pyran-4-yl)methyl)-5,6,7,8-tetrahydroimidazo[1,5-a]pyrazin-3-amine,
N-phenyl-7-((tetrahydro-2H-pyran-4-yl)methyl)-5,6,7,8-tetrahydroimidazo[1,5-a]pyrazin-3-amine,
7-benzyl-N-(2-fluorophenyl)-5,6,7,8-tetrahydroimidazo[1,5-a]pyrazin-3-amine,
N-(4-((3-(phenylamino)-5,6-dihydroimidazo[1,5-a]pyrazin-7(8H)-yl)methyl)phenyl)acetamide, N-(3-methoxyphenyl)-8-((tetrahydro-2H-pyran-4-yl) methyl)-6,7,8,9-tetrahydro-5H-imidazo[1,5-a][1,4]diazepin-3-amine,
N-(4-fluorophenyl)-8-((tetrahydro-2H-pyran-4-yl) methyl)-6,7,8,9-tetrahydro-5H-imidazo[1,5-a][1,4]diazepin-3-amine,
N-(3-chloro-2-fluorophenyl)-8-((tetrahydro-2H-pyran-4-yl)methyl)-6,7,8,9-tetrahydro-5H-imidazo[1,5-a][1,4]diazepin-3-amine,
N-(3,5-difluorophenyl)-8-((tetrahydro-2H-pyran-4-yl) methyl)-6,7,8,9-tetrahydro-5H-imidazo[1,5-a][1,4]diazepin-3-amine,
3-(7-benzyl-5,6,7,8-tetrahydroimidazo[1,5-a]pyrazin-3-ylamino)phenol,
7-(4-fluorobenzyl)-N-(5-fluoropyridin-2-yl)-5,6,7,8-tetrahydroimidazo[1,5-a]pyrazin-3-amine,
7-benzyl-N-(4-fluorophenyl)-5,6,7,8-tetrahydroimidazo [1,5-a]pyrazin-3-amine,
N-(2-bromo-6-chlorophenyl)-8-((tetrahydro-2H-pyran-4-yl)methyl)-6,7,8,9-tetrahydro-5H-imidazo[1,5-a][1,4]diazepin-3-amine,
N-(7-benzyl-5,6,7,8-tetrahydroimidazo[1,5-a]pyrazin-3-yl)-N-phenylpropionamide,
N-(7-benzyl-5,6,7,8-tetrahydroimidazo[1,5-a]pyrazin-3-yl)-N-(3-hydroxyphenyl)propionamide,
N-(3-hydroxyphenyl)-N-(7-phenethyl-5,6,7,8-tetrahydroimidazo[1,5-a]pyrazin-3-yl)propionamide,
7-benzyl-N-methyl-N-phenyl-5,6,7,8-tetrahydroimidazo [1,5-a]pyrazin-3-amine,
N-benzyl-7-(cyclohexylmethyl)-5,6,7,8-tetrahydroimidazo[1,5-a]pyrazin-3-amine,
3-benzyl-7-(cyclohexylmethyl)-5,6,7,8-tetrahydroimidazo[1,5-a]pyrazine trifluoroacetate,
3-(4-fluorobenzyl)-7-((tetrahydro-2H-pyran-4-yl) methyl)-5,6,7,8-tetrahydroimidazo[1,5-a]pyrazine hydrochloride,
7-(cyclohexylmethyl)-3-(4-fluorobenzyl)-5,6,7,8-tetrahydroimidazo[1,5-a]pyrazine hydrochloride,
7-phenethyl-N-phenyl-5,6,7,8-tetrahydroimidazo[1,5-a] pyrazin-3-amine,
N-phenyl-7-(tetrahydro-2H-pyran-4-yl)-5,6,7,8-tetrahydroimidazo[1,5-a]pyrazin-3-amine,
N-phenyl-7-(pyridin-4-ylmethyl)-5,6,7,8-tetrahydroimidazo[1,5-a]pyrazin-3-amine,
3-(7-phenethyl-5,6,7,8-tetrahydroimidazo[1,5-a]pyrazin-3-ylamino)phenol,
7-(2,4-difluorobenzyl)-N-(4-fluorophenyl)-5,6,7,8-tetrahydroimidazo[1,5-a]pyrazin-3-amine,
7-((4,4-difluorocyclohexyl)methyl)-N-(4-fluorophenyl)-5,6,7,8-tetrahydroimidazo[1,5-a]pyrazin-3-amine,
N-(4-fluorophenyl)-7-((5-fluoropyridin-2-yl)methyl)-5,6,7,8-tetrahydroimidazo[1,5-a]pyrazin-3-amine,
N-(4-fluorophenyl)-7-((6-fluoropyridin-3-yl)methyl)-5,6,7,8-tetrahydroimidazo[1,5-a]pyrazin-3-amine,
N-(4-fluorophenyl)-7-((6-methoxypyridin-3-yl)methyl)-5,6,7,8-tetrahydroimidazo[1,5-a]pyrazin-3-amine,
7-cyclohexyl-N-(4-fluorophenyl)-5,6,7,8-tetrahydroimidazo[1,5-a]pyrazin-3-amine,
7-(3-methoxyphenethyl)-N-phenyl-5,6,7,8-tetrahydroimidazo[1,5-a]pyrazin-3-amine,
7-(4-methoxyphenethyl)-N-phenyl-5,6,7,8-tetrahydroimidazo[1,5-a]pyrazin-3-amine,
7-(3-(3-methoxyphenyl)propyl)-N-phenyl-5,6,7,8-tetrahydroimidazo[1,5-a]pyrazin-3-amine,
7-(3-(4-methoxyphenyl)propyl)-N-phenyl-5,6,7,8-tetrahydroimidazo[1,5-a]pyrazin-3-amine,
3-(2-(3-(phenylamino)-5,6-dihydroimidazo[1,5-a] pyrazin-7(8H)-yl)ethyl)phenol,
4-(2-(3-(phenylamino)-5,6-dihydroimidazo[1,5-a] pyrazin-7(8H)-yl)ethyl)phenol,
3-(3-(3-(phenylamino)-5,6-dihydroimidazo[1,5-a] pyrazin-7(8H)-yl)propyl)phenol,
4-(3-(3-(phenylamino)-5,6-dihydroimidazo[1,5-a] pyrazin-7(8H)-yl)propyl)phenol,
or a pharmaceutically acceptable salt or solvate thereof.

Any compound referred to herein is intended to represent such specific compound as well as certain variations or forms. In particular, compounds referred to herein may have asymmetric centers and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

In another aspect, the invention refers to the processes for obtaining the compounds of general formula (I).

Compounds of formula (I) as defined above are prepared starting from compounds of formula (II):

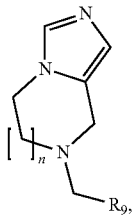

(II)

wherein n and $R_9$ have the same meaning than above, which react with an azidating agent, for example p-$C_{12}$($C_6H_4$)$SO_2N_3$, in the presence of an organic base, such as for example nBuLi, in an inert organic solvent, in particular as THF, at low temperatures, preferably at about −78° C., to give compounds of formula (III):

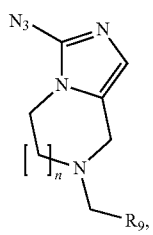

(III)

wherein n and $R_9$ are as defined above, which are submitted to a reduction by hydrogenation under a hydrogen atmosphere with a suitable catalyst, preferably palladium in an organic solvent such as ethanol, methanol, ethyl acetate or a mixture of two of them, or alternatively, in the presence of a suitable reducing agent as a metallic hydride, preferably lithium aluminium hydride in an organic solvent, such as diethyl ether, to give compounds of formula (IV):

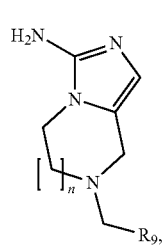

(IV)

wherein n and $R_9$ are as defined above, which may be reacted with an isocyanate of formula $R_3$—N=C=O, $R_3$ being as defined above for formula (I), to give bisureas of formula (V):

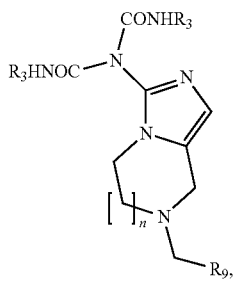

(V)

wherein n, $R_3$ and $R_9$ are as defined above, which are reacted with a base, such as $K_2CO_3$, in the presence of an organic solvent, preferably a polar solvent such as MeOH, to yield compounds of formula (Ia):

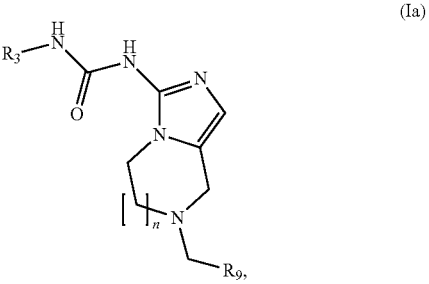

(Ia)

a particular case of compounds of formula (I) according to the present invention in which $R_1$ represents a —NHCONHR$_3$ group and n, $R_3$ and $R_9$ are as defined for formula (I) above, or, compounds of formula (IV) as defined above which are acylated by a compound of formula $R_3$COX where X is an halogen atom and $R_3$ is as defined above for formula (I), preferably in an aprotic solvent such as dichloromethane, toluene or tetrahydrofuran in the presence of an organic base such as N,N-diisopropylethylamine or pyridine, to yield compounds of formula (Ib):

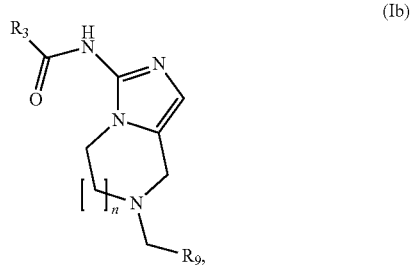

(Ib)

a particular case of compounds of formula (I) according to the present invention in which $R_1$ represents a —NR$_4$COR$_3$ group, $R_4$ represents a hydrogen atom, and n, $R_3$ and $R_9$ are as defined for formula (I) above, or, compounds of formula (IV) as defined above which are reacted with a compound of formula $R_{71}$X where X is an halogen atom, and $R_{71}$ is selected from the group consisting of a substituted or unsubstituted aryl group and substituted or unsubstituted heteroaryl group, in an aprotic inert organic solvent such as toluene or dioxane, in the presence of a palladium catalyst such as Pd$_2$(dba)$_3$, and an organophosphorous ligand such as Xantphos or BrettPhos and a base such as KOtBu or NaOtBu, to yield compounds of formula (Ic):

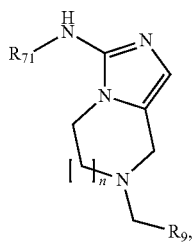

(Ic)

a particular case of compounds of formula (I) according to the present invention in which $R_1$ represents a $-NR_{71}R_{72}$ group, $R_{71}$ is selected from the group consisting of a substituted or unsubstituted aryl group and substituted or unsubstituted heteroaryl group, $R_{72}$ represents a hydrogen atom, and n and $R_9$ are as defined above for formula (I), compounds of formula (Ic) which may be submitted to an acylation reaction with a compound of formula $R_3COX$ where X is an halogen atom and $R_3$ is as defined above for formula (I), preferably in an aprotic solvent such as dichloromethane, toluene or tetrahydrofuran in the presence of an organic base such as N,N-diisopropylethylamine or pyridine, to yield compounds of formula (Id):

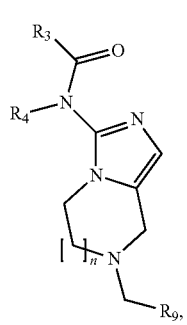

(Id)

a particular case of compounds of formula (I) according to the present invention in which $R_1$ represents a $-NR_4COR_3$ group, n, $R_3$ and $R_9$ are as defined above for formula (I), and $R_4$ is selected from the group consisting of a substituted or unsubstituted aryl group and substituted or unsubstituted heteroaryl group, compounds of formula (Ic) which may be reacted with a compound of formula $R_{72}X$ where X is an halogen atom, and $R_{72}$ is a linear or branched, substituted or unsubstituted $C_{1-3}$ aliphatic radical, in an aprotic polar organic solvent such as dimethylformamide in the presence of a base such as sodium hydride to yield compounds of formula (Ie):

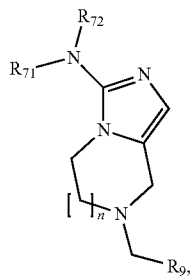

(Ie)

a particular case of compounds of formula (I) according to the present invention in which $R_1$ represents a $-NR_{71}R_{72}$ group, $R_{71}$ is selected from the group consisting of a substituted or unsubstituted aryl group and substituted or unsubstituted heteroaryl group, $R_{72}$ represents a linear or branched, substituted or unsubstituted $C_{1-3}$ aliphatic radical, and n and $R_9$ are as defined above for formula (I), compounds of formula (Ic), which, in the case where $R_9$ represents a phenyl group, may be debenzylated following known methods in the art, such as hydrogenation under palladium catalysis in the presence of an organic solvent such as ethyl alcohol to give compounds of formula (VI):

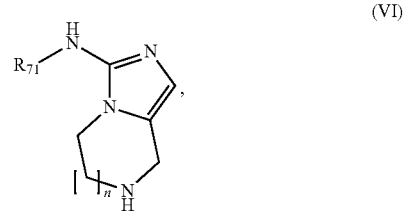

(VI)

wherein $R_{71}$ is selected from the group consisting of a substituted or unsubstituted aryl group and substituted or unsubstituted heteroaryl group, and n is as defined above, which are then submitted to a reductive amination process by reaction with aldehydes or ketones of formula $R_2=O$, where $R_2$ is as defined above, in the presence of a reducing agent such as $NaBH(OAc)_3$ in an inert organic solvent such as THF or acetonitrile, to yield compounds of formula (If):

(If)

a particular case of compounds of formula (I) according to the present invention in which $R_1$ represents a $-NR_{71}R_{72}$ group, $R_{71}$ is selected from the group consisting of a substituted or unsubstituted aryl group and substituted or unsubstituted heteroaryl group, $R_{72}$ represents a hydrogen atom, and, n and $R_2$ are as defined above for formula (I).

Compounds of formula (I) as defined above may also be prepared starting from compounds of formula (IV) as defined above which are then submitted to a reductive amination process by reaction with aldehydes or ketones of formula $R_{71}=O$ where $R_{71}$ represents a linear or branched, substituted or unsubstituted $C_{1-10}$ aliphatic radical, a substituted or unsubstituted cycloalkyl group, a substituted or unsubstituted cycloalkylalkyl group, a substituted or unsubstituted arylalkyl group, a substituted or unsubstituted heterocycloalkyl group, a substituted or unsubstituted heterocycloalkylalkyl group, or a unsubstituted heteroarylalkyl group, in the presence of a reducing agent such as $NaBH(OAc)_3$ in an inert organic solvent such as THF or acetonitrile, to yield compounds of formula (Ig):

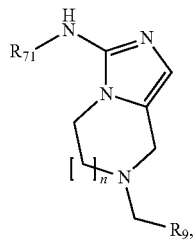

(Ig)

a particular case of compounds of formula (I) according to the present invention in which $R_1$ represents a $-NR_{71}R_{72}$ group, $R_{71}$ is selected from the group consisting of a linear or branched, substituted or unsubstituted $C_{1-10}$ aliphatic radical, a substituted or unsubstituted cycloalkyl group, a substituted or unsubstituted cycloalkylalkyl group, a substituted or unsubstituted arylalkyl group, a substituted or unsubstituted heterocycloalkyl group, a substituted or unsubstituted heterocycloalkylalkyl group, or a unsubstituted heteroarylalkyl group, $R_{72}$ represents a hydrogen atom, and n and $R_9$ are as defined above for formula (I).

Compounds of formula (I) as defined above may alternatively be prepared starting from compounds of formula (II) as defined above which react with a compound of formula $R_6-(C(R_{51}R_{52}))_{(m')}-CHO$ where $R_6$, $R_{51}$, $R_{52}$ are as defined above and m' is 0, 1 or 2, to give compounds of formula (VII):

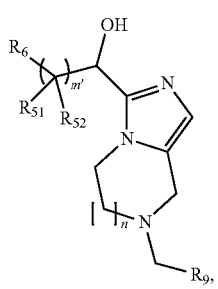

(VII)

wherein $R_{51}$, $R_{52}$, $R_6$, $R_9$, m' and n are as defined above, which are reduced in the presence of an organosilane, such as triethylsilane, and an acid, such as trifluoroacetic acid, to yield compounds of formula (Ih):

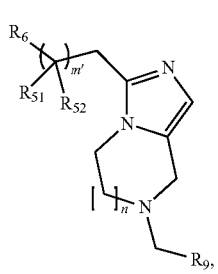

(Ih)

a particular case of compounds of formula (I) of the present invention in which $R_1$ represents $R_6-(C(R_{51}R_{52}))m'-CH_2-$, and $R_{51}$, $R_{52}$, $R_6$, $R_9$, m' and n are as defined above.

In the process described above, aldehydes or ketones of formula $R_2=O$ or $R_{71}=O$ mean that the carbonyl group is formed on any carbon atom of the groups defined for $R_2$ and $R_{71}$ respectively in formula (I) above.

Compounds of formula (II) are prepared by known methods, and in particular starting from compounds of formula (VIII):

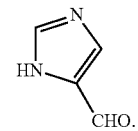

(VIII)

which are reacted with a compound of formula $HO-CH_2-(CH_2)_n-NH-CH_2-R_9$ where $R_9$ and n are as defined for formula (I) above, in the presence of a reducing agent, such as $NaBH(OAc)_3$ in an inert organic solvent, such as THF or acetonitrile, to give compounds of formula (IXa):

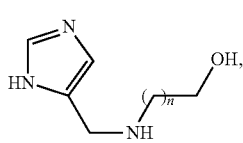

(IXa)

where $R_9$ and n are as defined above,
or alternatively, which react with a compound of formula $HO-CH_2-(CH_2)n-NH_2$ in the same condition, to give compounds of formula (IXb):

(IXb)

where n is as defined above,
which are then submitted to a second reductive amination in the presence of $R_9-CHO$ in which $R_9$ is as defined above, to give a compound of formula (IXa) as defined above, compounds of formula (IXa) which react with thionyl chloride to give the corresponding compounds (Xa):

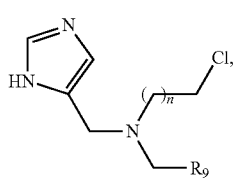

(Xa)

which are submitted to a cyclisation reaction in the presence of an organic base such as triethylamine in an organic solvent such as acetonitrile, in a range of temperature from about 25° C. to reflux, to yield compounds of formula (II) as defined above:

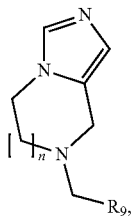

(II)

where n is as defined above.

Starting compounds of the above mentioned processes of synthesis are either commercially available, or easily prepared by known methods to the skilled artisan.

An additional aspect of the invention relates to the therapeutic use of the compounds of general formula (I). As mentioned above, compounds of general formula (I) show a strong affinity to σ receptors and can behave as agonists, antagonists, inverse agonists, partial antagonists or partial agonists thereof. Preferably they behave as antagonists, in particular antagonists of the $\sigma_1$ receptor. Therefore, compounds of general formula (I) are useful as medicaments.

They are suitable for the treatment and the prophylaxis of disorders and diseases mediated by σ receptors, especially, $\sigma_1$ receptors. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, pain, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

In another preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment and prophylaxis of disorders and diseases mediated by σ receptors, as explained before.

In particular the invention refers to the use of compounds of formula (I) for the manufacture of a medicament for the treatment and prophylaxis of diarrhoea, lipoprotein disorders, hyperlipidemia, hypertriglyceridemia, hypercholesterolemia, obesity, migraine, pain, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

Especially, the invention refers to the use of compounds of formula (I) for the manufacture of a medicament for the treatment and prophylaxis of pain, especially neuropathic pain, inflammatory pain or other pain conditions involving allodynia and/or hyperalgesia, and more preferably medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

A further related aspect of the present invention relates to a method of treating or preventing disorders and diseases mediated by σ receptors which method comprises administering to a patient in need of such a treatment a therapeutically effective amount of a compound as above defined or a pharmaceutical composition thereof. Preferably the disorders and diseases mediated by σ receptors are chosen among the pain syndromes, and especially medium to severe pain, visceral pain, chronic pain, chronic pain, cancer pain, migraine, inflammatory pain, acute pain or neuropathic pain, allodynia or hyperalgesia, whereas this could also include mechanical allodynia or thermal hyperalgesia.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants.

In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, dragées, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

Preparation A 8-(Cyclohexylmethyl)-6,7,8,9-tetrahydro-5H-imidazo[1,5-a][1,4]diazepine A.1. 3-((1H-Imidazol-4-yl)methylamino)propan-1-ol

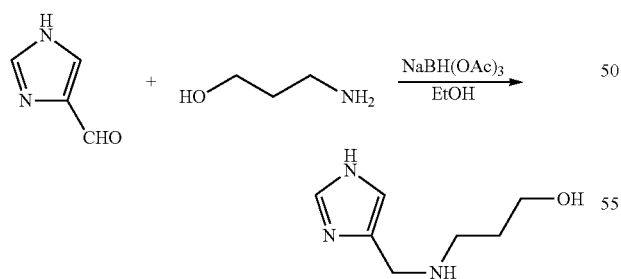

1H-Imidazole-4-carbaldehyde (2.96 g, 30.8 mmol) was suspended in absolute ethanol (50 mL) and 3-aminopropan-1-ol (2.36 mL, 30.8 mmol) was added. After 2.5 h of stirring at room temperature the imine formation was complete as judged by proton NMR. After cooling the mixture to 0° C., sodium triacetoxyborohydride (32.6 g, 154 mmol) was added portionwise followed by extra ethanol (75 mL). The cooling bath was removed and the mixture was stirred overnight. LC/MS showed complete reduction and the mixture corresponding to the title compound was employed directly in the next step.

LC/MS m/z 156 [M+H]$^+$.

A.2. 3-(((1H-Imidazol-4-yl)methyl)(cyclohexylmethyl)amino)-propan-1-ol

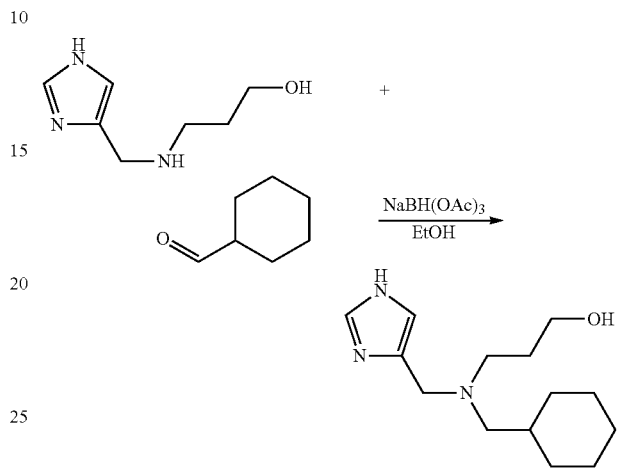

The crude mixture of 3-((1H-imidazol-4-yl)methylamino) propan-1-ol (~30.8 mmol in 125 mL absolute ethanol) was treated with cyclohexanecarbaldehyde (10.40 g, 93 mmol) and stirred for 2.5 h at room temperature. Then the mixture was cooled in an ice-bath and sodium triacetoxyborohydride (32.6 g, 154 mmol) was added followed by additional 30 mL of absolute ethanol. The mixture was allowed to warm to room temperature and then stirred for 1 h. After quenching with water the mixture was rendered neutral with 1M aqueous sodium hydroxide. Ethanol was removed on a rotavapor and the residue was extracted with ethyl acetate to remove some impurities. The aqueous layer was further basified with to pH ~14 and extracted three times with ethyl acetate. The combined organic layers were washed with brine, dried over sodium sulfate, filtered and concentrated. The crude title compound (5.73 g), obtained as nearly colourless oil, showed sufficient purity to be employed in the next step.

$^1$H NMR (CDCl$_3$) δ 7.62-7.55 (m, 1H), 6.93 (s, 1H), 3.83-3.74 (m, 2H), 3.59 (s, 2H), 2.73-2.63 (m, 2H), 2.27 (d, J=7.1 Hz, 2H), 1.80-1.46 (m, 9H), 1.30-1.05 (m, 4H), 0.94-0.75 (m, 2H).

LC/MS m/z 252 [M+H]$^+$.

A.3. N-((1H-Imidazol-4-yl)methyl)-3-chloro-N-(cyclohexylmethyl)-propan-1-amine dihydrochloride

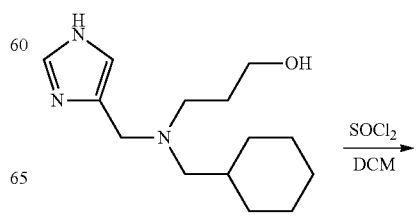

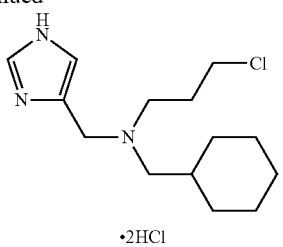

•2HCl 3-(((1H-Imidazol-4-yl)methyl)(cyclohexylmethyl)amino)propan-1-ol (5.73 g, 19.83 mmol) was dissolved in dichloromethane (110 mL) under a nitrogen atmosphere. After cooling down to ~0° C. thionyl chloride (5.79 mL, 79 mmol) was added dropwise, then the mixture was stirred overnight at room temperature. Next, additional 4 equivalents of SOCl$_2$ were added in two portions driving the reaction to completion after overnight stirring. After stripping with dichloromethane the crude title compound (~6.2 g) was obtained as yellow foam.

LC/MS m/z 270 & 272 [M+H]$^+$.

A.4. 8-(Cyclohexylmethyl)-6,7,8,9-tetrahydro-5H-imidazo[1,5-a][1,4]diazepine

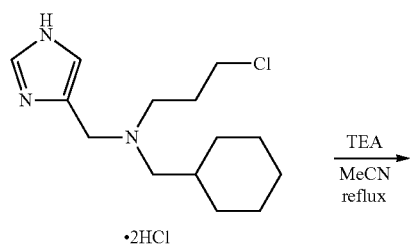

•2HCl

TEA
MeCN
reflux

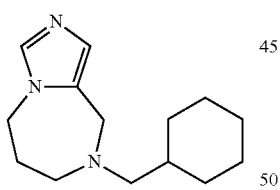

N-((1H-Imidazol-4-yl)methyl)-3-chloro-N-(cyclohexylmethyl)propan-1-amine dihydrochloride (19.8 mmol, 6.80 g) was suspended in acetonitrile (dry, 130 mL). The suspension was placed under a nitrogen atmosphere and triethylamine (10 mL, 71.7 mmol) was added. The reaction mixture was heated at reflux for ~5 h and then stirred at room temperature overnight. After concentration the product was purified by flash column chromatography to give the title compound (1.73 g).

$^1$H NMR (CDCl$_3$) δ 7.37 (d, J=1.2 Hz, 1H), 6.85 (s, 1H), 4.07-4.02 (m, 2H), 3.80 (s, 2H), 3.08 (distorted dd, J=6.5, 3.8 Hz, 2H), 2.11 (d, J=7.1 Hz, 2H), 1.85-1.60 (m, 7H), 1.47-1.35 (m, 1H), 1.30-1.07 (m, 3H), 0.89-0.75 (m, 2H).

LC/MS m/z 234 [M+H]$^+$.

Preparation B

7-Benzyl-5,6,7,8-tetrahydroimidazo[1,5-a]pyrazine

B.1. 2-(((1H-Imidazol-4-yl)methyl)(benzyl)amino)ethanol

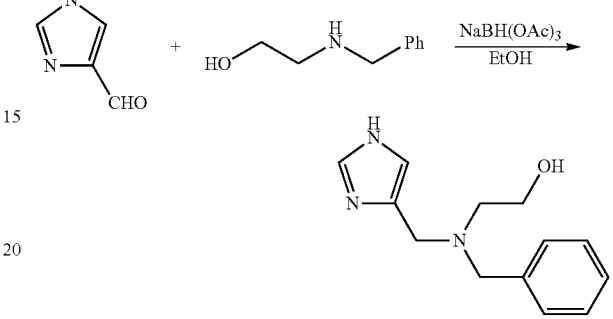

A 1 litre flask was charged with 1H-imidazole-4-carbaldehyde (14 g, 146 mmol) and absolute ethanol (240 mL). Then 2-(benzylamino)ethanol (20.8 mL, 146 mmol) was added and the white suspension turned slowly into a yellow solution after 3 h The mixture was then cooled in an ice-bath and sodium triacetoxyborohydride (93 g, 437 mmol) was added portionwise. The mixture was then stirred overnight at room temperature. Water was added and the mixture was partially concentrated. After neutralising to pH ~7 with 1M aqueous NaOH, the aqueous phase was rinsed twice with ethyl acetate, then it was basified further to pH 14. The aqueous layer was then extracted with thrice with ethyl acetate. The combined organic layers were dried over sodium sulfate, filtered and evaporated to dryness to give the title compound (26.9 g), which was directly used in the next step.

$^1$H NMR (CDCl$_3$) δ 7.52 (s, 1H), 7.37-7.18 (m, 6H), 6.87 (s, 1H), 3.69 (s, 2H), 3.68-3.58 (m, 5H), 2.70 (t, J=5.1 Hz, 2H).

LC/MS: m/z 232 [M+H]$^+$.

B.2 N-((1H-Imidazol-4-yl)methyl)-N-benzyl-2-chloroethanamine dihydrochloride

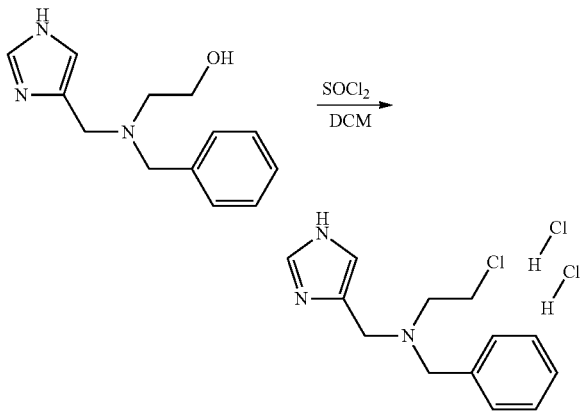

2-(((1H-Imidazol-4-yl)methyl)(benzyl)amino)ethanol (~112 mmol) was dissolved in dichloromethane (600 mL) and the solution was placed under a nitrogen atmosphere. After cooling in ice-bath, thionyl chloride (33 mL, 452 mmol) was added dropwise. Upon completing the addition the mixture was allowed to stir at room temperature for 3 days. Then it was concentrated and coevaporated with dichloromethane to give the title compound as a dark yellow solid (47 g).

$^1$H NMR (DMSO) δ 9.22 (s, 1H), 7.91 (br s, 1H), 7.64 (br s, 2H), 7.43 (br s, 3H), 4.67-4.20 (m, 5H), 3.99 (br s, 2H), 3.22 (br s, 2H).

LC/MS m/z 250 & 252 [M+H]$^+$.

B.3.
7-Benzyl-5,6,7,8-tetrahydroimidazo[1,5-a]pyrazine

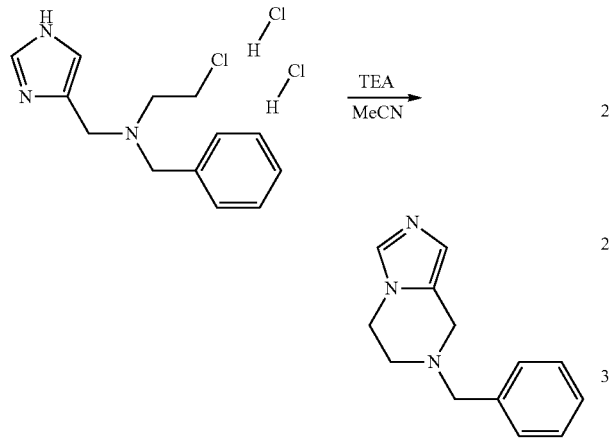

N-((1H-Imidazol-4-yl)methyl)-N-benzyl-2-chloroethanamine dihydrochloride (46.2 g, ~95 mmol) was suspended in anhydrous acetonitrile (900 mL) and the solution was placed under nitrogen atmosphere. Triethylamine (46.1 mL, 331 mmol) was added and the mixture was refluxed overnight. The dark reaction mixture was cooled down, concentrated and then diluted with dichloromethane and saturated aqueous sodium carbonate. Extraction provided the crude product, that was purified by column chromatography using a gradient of methanol in ethyl acetate, to give the title compound as an orange solid (12.7 g).

$^1$H NMR (CDCl$_3$) δ 7.40 (s, 1H), 7.39-7.27 (m, 5H), 6.74 (s, 1H), 4.04 (t, J=5.4 Hz, 2H), 3.70 (s, 2H), 3.67 (s, 2H), 2.84 (t, J=5.7 Hz, 2H).

LC/MS m/z 214 [M+H]$^+$.

Preparation C 7-(Cyclohexylmethyl)-5,6,7,8-tetrahydroimidazo[1,5-a]pyrazine

C.1. 5,6,7,8-Tetrahydroimidazo[1,5-a]pyrazine

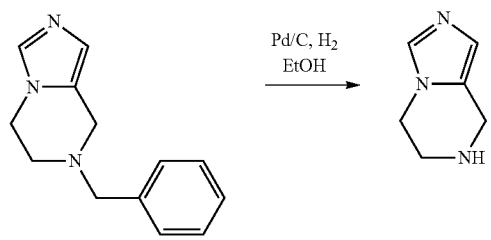 [SMILES: c1ccc(CN2CCn3cncc3C2)cc1 ; c1ncn2c1CNCC2]

7-Benzyl-5,6,7,8-tetrahydroimidazo[1,5-a]pyrazine (4.89 g, 22.9 mmol) was dissolved in absolute ethanol (200 mL) and 10% palladium on carbon (4.88 g) was added to the solution. The mixture was placed under 1 bar of a hydrogen atmosphere and stirred vigorously overnight. Then it was filtered through celite rinsing with ethanol, concentrated and coevaporated with dichloromethane. The title compound was obtained as off-white oil (2.52 g).

$^1$H NMR (CDCl$_3$) δ 7.42 (s, 1H), 6.77 (s, 1H), 4.07 (s, 2H), 3.99 (t, J=5.6 Hz, 2H), 3.22 (t, J=5.6 Hz, 2H), 1.76 (br s, 1H).

LC/MS m/z 124 [M+H]$^+$.

C.2. 7-(Cyclohexylmethyl)-5,6,7,8-tetrahydroimidazo[1,5-a]pyrazine

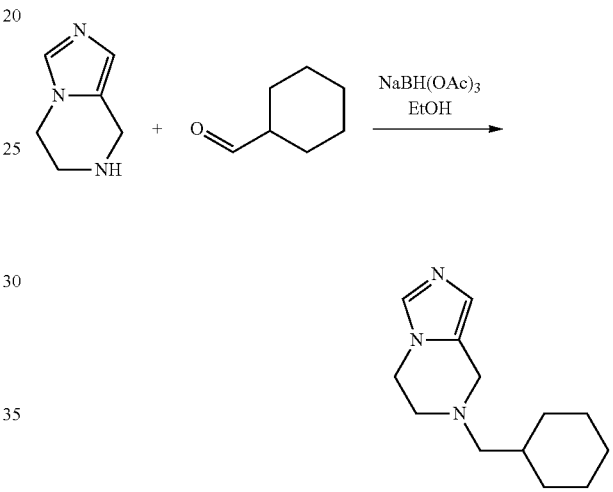

5,6,7,8-Tetrahydroimidazo[1,5-a]pyrazine (1.0 g, 7.71 mmol) was dissolved in absolute ethanol (50 mL) and the solution was placed under a nitrogen atmosphere. Cyclohexanecarbaldehyde (1.86 mL, 15.4 mmol) was added and the reaction mixture was stirred 2 h at room temperature. Then it was cooled in an ice-bath and sodium triacetoxyhydroborate (6.54 g, 30.9 mmol) was added portionwise. Stirring was continued at room temperature overnight, after which the reaction mixture was concentrated and partitioned between dichloromethane and water. After separation of the layers, the aqueous layer was basified to pH ~14. and it was extracted with dichloromethane three times. The combined extracts were dried over sodium sulfate, filtered and concentrated. Flash chromatography (gradient of methanol in dichloromethane) gave the title compound as a light yellow solid (1.82 g).

$^1$H NMR (CDCl$_3$) δ 7.51 (s, 1H), 6.78 (s, 1H), 4.05 (t, J=5.5 Hz, 2H), 3.61 (s, 2H), 2.79 (t, J=5.5 Hz, 2H), 2.32 (d, J=7.2 Hz, 2H), 1.85-1.62 (m, 5H), 1.60-1.46 (m, 1H), 1.32-1.10 (m, 3H), 0.98-0.82 (m, 2H).

LC/MS m/z 220 [M+H]$^+$.

Example 1

1-(8-(Cyclohexylmethyl)-6,7,8,9-tetrahydro-5H-imidazo[1,5-a][1,4]diazepin-3-yl)-3-ethylurea

1.1 3-Azido-8-(cyclohexylmethyl)-6,7,8,9-tetrahydro-5H-imidazo[1,5-a][1,4]diazepine

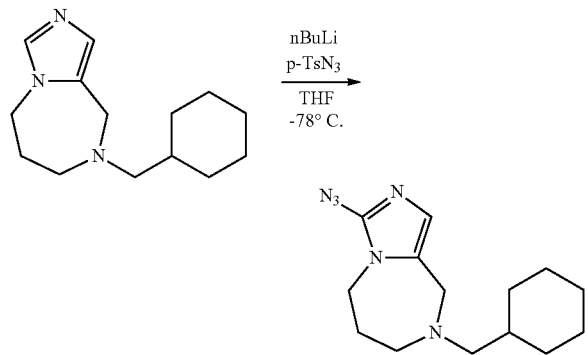

8-(Cyclohexylmethyl)-6,7,8,9-tetrahydro-5H-imidazo[1,5-a][1,4]diazepine, described in preparation A, (1.883 g, 7.1 mmol) was dissolved in dry tetrahydrofuran (35 mL) and cooled to −78° C. under an atmosphere of nitrogen. N-Butyllithium (4.88 mL of 1.6M solution in hexanes, 7.81 mmol) was then added dropwise. After 30 minutes 4-methylbenzenesulfonyl azide (9.57 g, 7.28 mmol, 15 wt % solution in toluene) was added dropwise and the mixture, was stirred for 1 h at −78° C. Next, the mixture was quenched with water and allowed to stir overnight at room temperature. The mixture was extracted with ethyl acetate from diluted aqueous sodium carbonate, the organic extracts washed with brine, dried over sodium sulphate, filtered and evaporated to dryness. The crude was purified on silica (gradient of methanol in dichloromethane) to give the title compound as an orange oil (0.92 g).

LC/MS m/z 275 [M+H]$^+$.

1.2. 8-(Cyclohexylmethyl)-6,7,8,9-tetrahydro-5H-imidazo[1,5-a][1,4]diazepin-3-amine

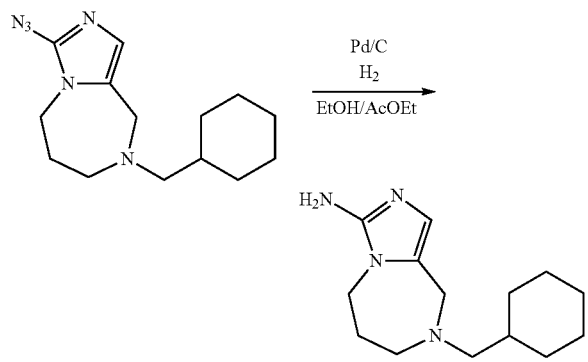

3-Azido-8-(cyclohexylmethyl)-6,7,8,9-tetrahydro-5H-imidazo[1,5-a][1,4]diazepine (1.078 g, 3.3 mmol) was dissolved in a mixture of ethanol (25 mL) and ethyl acetate (25 mL). The solution was subjected to hydrogenolysis using 10% palladium on carbon under 1 bar of hydrogen at 60° C. for 2 h. Then the mixture was filtered through celite and evaporated to dryness. Flash column on silica gel (gradient of 7N methanolic ammonia in dichloromethane) gave the title compound as a yellow solid (0.69 g).

LC/MS mass 249 [M+H]$^+$.

1.3 1-(8-(Cyclohexylmethyl)-6,7,8,9-tetrahydro-5H-imidazo[1,5-a][1,4]diazepin-3-yl)-3-ethylurea

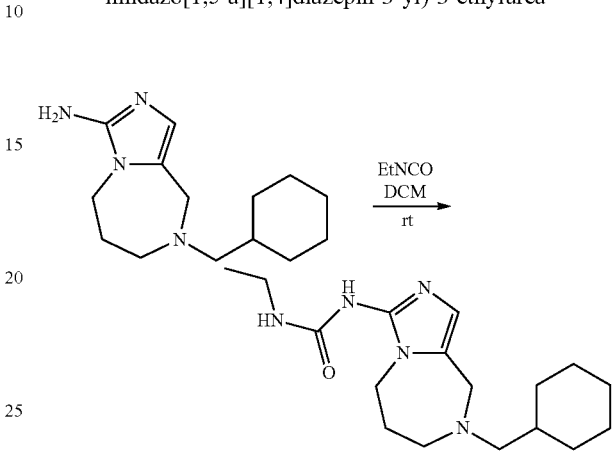

8-(Cyclohexylmethyl)-6,7,8,9-tetrahydro-5H-imidazo[1,5-a][1,4]diazepin-3-amine (0.279 g, 1.0 mmol) was dissolved in dichloromethane (dry, 10 mL) under an atmosphere of nitrogen. The solution was treated with the solution of isocyanatoethane (0.095 mL, 1.200 mmol) in dichloromethane (dry, 1 mL) and stirred for 2 days at room temperature controlling the progress of the reaction. The mixture was then quenched with methanol. Purification by first straight phase and then reversed phase column chromatography provided the title compound as a white solid (86 mg).

$^1$H NMR (CDCl$_3$) δ: 6.48 (s, 1H), 4.18-3.88 (m, 2H), 3.70 (s, 2H), 3.38-3.22 (m, 2H), 3.04 (dd, J=6.9, 3.5 Hz, 2H), 2.14 (d, J=7.0 Hz, 2H), 1.87-1.56 (m, 7H), 1.48-1.30 (m, 1H), 1.30-1.08 (m, 3H), 1.19 (t, J=7.2 Hz, 3H), 0.82 (qd, J=13.7, 12.7, 3.5 Hz, 2H).

LC/MS m/z 320 [M+H]$^+$.

Example 2

1-(7-(Cyclohexylmethyl)-5,6,7,8-tetrahydroimidazo[1,5-a]pyrazin-3-yl)-3-ethylurea

2.1 3-Azido-7-(cyclohexylmethyl)-5,6,7,8-tetrahydroimidazo[1,5-a]pyrazine

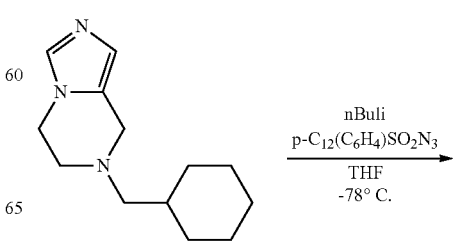

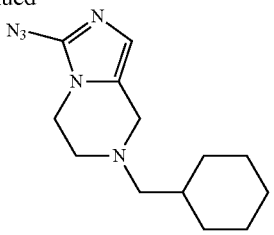

7-(Cyclohexylmethyl)-5,6,7,8-tetrahydroimidazo[1,5-a]pyrazine (1.120 g, 4.7 mmol), described in preparation C, was dissolved in dry tetrahydrofuran (20 mL) under an atmosphere of nitrogen and the solution was cooled to −78° C. n-Butyllithium in hexanes (3.08 mL, 4.94 mmol) was added dropwise followed after 1 h by 4-dodecylbenzenesulfonyl azide (mixture of isomers, 1.886 mL, 5.64 mmol) The cooling bath was removed and the mixture was allowed to warm up to room temperature while stirring for 2 h. Then the mixture was quenched with water, aqueous sodium bicarbonate was added and the mixture was extracted with ethyl acetate. The extracts were washed with water, then brine and dried over sodium sulfate. The crude product was purified by column chromatography using first a gradient of ethyl acetate in heptane, then of methanol in ethyl acetate. The title compound was obtained as a brown oil (0.55 g).

$^1$H NMR (CDCl$_3$) δ 6.60 (s, 1H), 3.98 (dd, J=11.0, 3.3 Hz, 2H), 3.72 (t, J=5.6 Hz, 2H), 3.57 (s, 2H), 3.39 (td, J=11.9, 1.9 Hz, 2H), 2.80-2.73 (m, 2H), 2.37 (d, J=7.2 Hz, 2H), 1.84-1.71 (m, 1H), 1.71-1.64 (m, 2H), 1.28 (qd, J=12.0, 4.4 Hz, 2H).

LC/MS m/z 262 [M+H]$^+$.

2.2 7-(Cyclohexylmethyl)-5,6,7,8-tetrahydroimidazo[1,5-a]pyrazin-3-amine

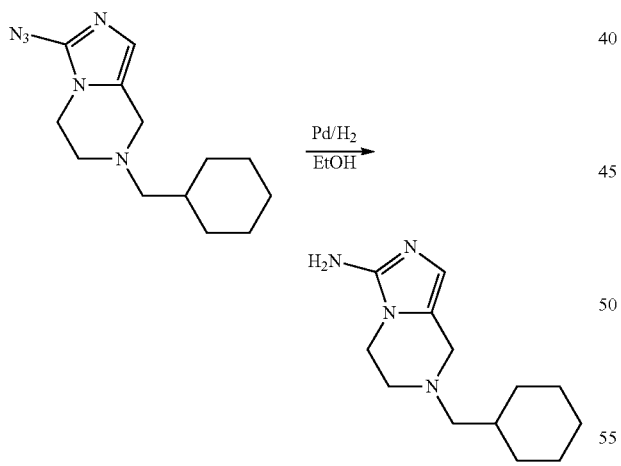

3-Azido-7-(cyclohexylmethyl)-5,6,7,8-tetrahydroimidazo[1,5-a]pyrazine (1.144 g, 4.35 mmol) was dissolved in ethyl acetate (25 mL) and ethanol (25 mL), 10% palladium on carbon (0.231 g, 0.218 mmol) was added and the mixture was subjected to hydrogenolysis under 1 bar of hydrogen for 3 h at room temperature. The mixture was then filtered through celite and the brown filtrate concentrated to dryness and the residue stripped twice with dichloromethane. The crude title compound (0.95 g) was employed as such in the next step.

$^1$H NMR (CDCl$_3$) δ 6.34 (s, 1H), 3.81 (br s, 2H), 3.69 (t, J=5.8 Hz, 2H), 3.52 (s, 2H), 2.77 (t, J=5.6 Hz, 2H), 2.29 (d, J=7.2 Hz, 2H), 2.01 (br s, 1H), 1.84-1.62 (m, 4H), 1.59-1.44 (m, 1H), 1.32-1.10 (m, 3H), 0.97-0.80 (m, 2H).

LC/MS m/z 235 [M+H]$^+$.

2.3 1-(7-(Cyclohexylmethyl)-5,6,7,8-tetrahydroimidazo[1,5-a]pyrazin-3-yl)-3-ethylurea

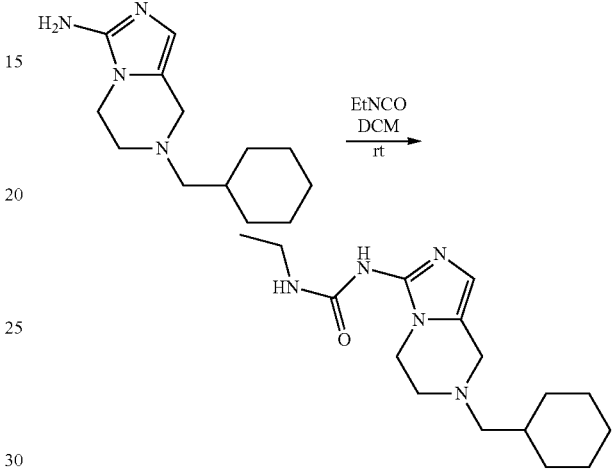

7-(Cyclohexylmethyl)-5,6,7,8-tetrahydroimidazo[1,5-a]pyrazin-3-amine (0.117 g, 0.50 mmol) was suspended in anhydrous dichloromethane (2 mL) under a nitrogen atmosphere and treated with isocyanatoethane (0.047 mL, 0.60 mmol). The stirring was continued overnight at room temperature. The mixture was then quenched with a few drops of methanol and purified by flash chromatography (gradient methanol in dichloromethane) to give the title compound as a pale yellow solid (48 mg).

$^1$H NMR (CDCl$_3$) δ: 9.13-8.21 (m, 2H), 6.42 (s, 1H), 3.84 (t, J=5.7 Hz, 2H), 3.52 (s, 2H), 3.33 (qd, J=7.2, 5.4 Hz, 2H), 2.78 (t, J=5.6 Hz, 2H), 2.29 (d, J=7.1 Hz, 2H), 1.84-1.61 (m, 5H), 1.59-1.43 (m, 1H), 1.33-1.08 (m, 3H), 1.19 (t, J=7.2 Hz, 3H), 0.89 (qd, J=11.8, 3.0 Hz, 2H).

LC/MS m/z 306 [M+H]$^+$.

Example 3

1-(7-(Cyclohexylmethyl)-5,6,7,8-tetrahydroimidazo[1,5-a]pyrazin-3-yl)-3-propylurea

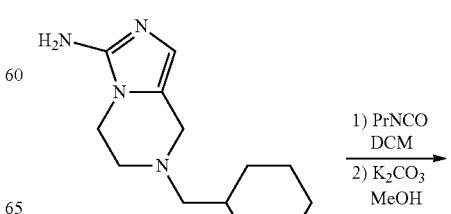

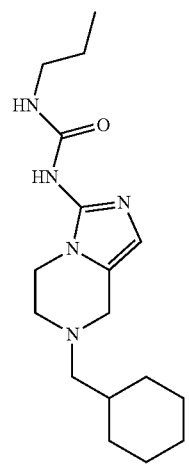

Example 5

7-(Cyclohexylmethyl)-N-phenyl-5,6,7,8-tetrahydroimidazo[1,5-a]pyrazin-3-amine

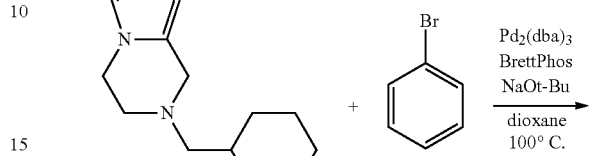

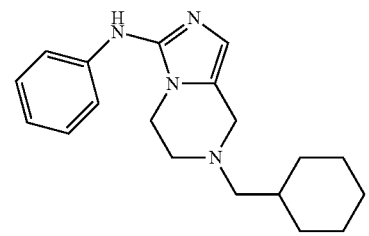

7-(Cyclohexylmethyl)-5,6,7,8-tetrahydroimidazo[1,5-a]pyrazin-3-amine (30 mg, 0.128 mmol), described in example 2.2, was dissolved in dry dichloromethane (1 mL) under a nitrogen atmosphere. n-Propyl isocyanate (73 μl, 0.768 mmol) was added and the orange solution was stirred at room temperature for 1 h giving almost a complete conversion towards a mixture of mono- and di-urea derivatives. The reaction mixture was concentrated and then the residue was redissolved in methanol (1 mL). An excess of solid potassium carbonate was added giving after 2 h of reaction almost exclusively the desired mono-urea product. The reaction mixture was concentrated and the residue diluted with water and extracted with dichloromethane. The crude product obtained after drying over sodium sulfate, filtration and solvent evaporation was purified using flash chromatography on silica using a gradient of ethyl acetate in dichloromethane, then of methanolic ammonia in ethyl acetate. A pure batch of the title compound was obtained (23 mg).

$^1$H NMR (CDCl$_3$) δ: 9.53-8.55 (m, 1H), 7.81-7.34 (m, 1H), 6.41 (s, 1H), 3.76 (t, J=5.6 Hz, 2H), 3.52 (s, 2H), 3.26 (q, J=6.7 Hz, 2H), 2.78 (t, J=5.7 Hz, 2H), 2.29 (d, J=7.2 Hz, 2H), 1.82-1.45 (m, 8H), 1.31-1.08 (m, 3H), 0.95 (t, J=7.4 Hz, 3H), 1.00-0.80 (m, 2H).

LC/MS m/z 320 [M+H]$^+$.

Example 4 was prepared following the same method as in example 3, using the appropriate isocyanate.

7-(Cyclohexylmethyl)-5,6,7,8-tetrahydroimidazo[1,5-a]pyrazin-3-amine (117 mg, 0.50 mmol) described in example 2.2, bromobenzene (63 μl, 0.60 mmol), dicyclohexyl(2',4',6'-triisopropyl-3,6-dimethoxybiphenyl-2-yl)phosphine (16 mg, 6 mol %), Pd$_2$(dba)$_3$ (6.9 mg, 1.5 mol %) and sodium tert-butoxide (58 mg, 0.60 mmol) were combined in a 8 mL vial, suspended in 1,4-dioxane (extra dry, 1 mL), and argon was passed through the mixture for a while. The vial was capped and stirred at 100° C. for 3 h. The mixture was then cooled down, diluted with dichloromethane and filtered through Celite. The concentrated filtrate was purified on a silica gel column (gradient of 10% methanol/ethyl acetate mixture in dichloromethane to give the title compound as an off-white solid (94 mg).

$^1$H NMR (CDCl$_3$) δ: 7.22 (t, J=7.9 Hz, 2H), 6.91-6.82 (m, 3H), 6.62 (s, 1H), 5.77 (s, 1H), 3.74 (t, J=5.6 Hz, 2H), 3.59 (s, 2H), 2.75 (t, J=5.6 Hz, 2H), 2.31 (d, J=7.2 Hz, 2H), 1.86-1.61 (m, 5H), 1.59-1.45 (m, 1H), 1.31-1.11 (m, 3H), 0.90 (qd, J=12.0, 3.2 Hz, 2H).

LC/MS m/z 311 [M+H]$^+$.

Examples 6-22 were prepared following the same method as in example 5, using the appropriate arylbromide.

| EX | Structure | Name | NMR |
|----|-----------|------|-----|
| 4 | 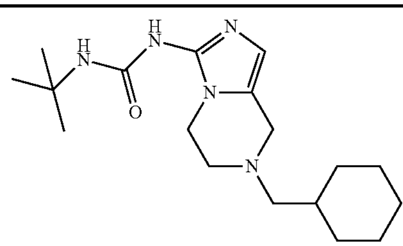 | 1-tert-butyl-3-(7-(cyclohexylmethyl)-5,6,7,8-tetrahydroimidazo[1,5-a]pyrazin-3-yl)urea | $^1$H NMR (CDCl$_3$) δ: 8.82 (s, 1H), 7.30-7.11 (m, 1H), 6.43 (s, 1H), 3.89-3.66 (m, 2H), 3.52 (s, 2H), 2.77 (t, J = 5.7 Hz, 2H), 2.28 (d, J = 7.2 Hz, 2H), 1.87-1.62 (m, 5H), 1.61-1.45 (m, 1H), 1.40 (s, 9H), 1.30-1.11 (m, 3H), 1.02-0.78 (m, 2H). |

| EX | Structure | Name | NMR |
|---|---|---|---|
| 6 | 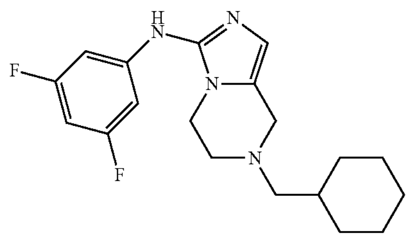 [SMILES: Fc1cc(F)cc(Nc2ncc3n2CCN(CC2CCCCC2)C3)c1] | 7-(cyclohexylmethyl)-N-(3,5-difluorophenyl)-5,6,7,8-tetrahydroimidazo[1,5-a]pyrazin-3-amine | $^1$H NMR (CDCl$_3$) δ: 6.64 (s, 1H), 6.44 (s, 1H), 6.43-6.31 (m, 2H), 6.27 (tt, J = 9.0, 2.3 Hz, 1H), 3.75 (t, J = 5.5 Hz, 2H), 3.59 (s, 2H), 2.76 (t, J = 5.5 Hz, 2H), 2.31 (d, J = 7.1 Hz, 2H), 1.86-1.63 (m, 5H), 1.61-1.43 (m, 1H), 1.33-1.09 (m, 3H), 0.98-0.80 (m, 2H). |
| 7 | 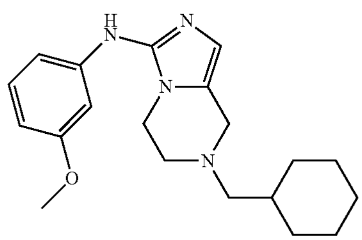 [SMILES: COc1cccc(Nc2ncc3n2CCN(CC2CCCCC2)C3)c1] | 7-(cyclohexylmethyl)-N-(3-methoxyphenyl)-5,6,7,8-tetrahydroimidazo[1,5-a]pyrazin-3-amine | $^1$H NMR (CDCl$_3$) δ: 7.12 (t, J = 8.1 Hz, 1H), 6.62 (s, 1H), 6.48-6.39 (m, 3H), 5.79 (s, 1H), 3.76 (s, 3H), 3.74 (t, J = 5.8 Hz, 2H), 3.58 (s, 2H), 2.74 (t, J = 5.6 Hz, 2H), 2.30 (d, J = 7.2 Hz, 2H), 1.86-1.63 (m, 5H), 1.60-1.44 (m, 1H), 1.32-1.09 (m, 3H), 0.89 (qd, J = 12.2, 3.2 Hz, 2H). |
| 8 | 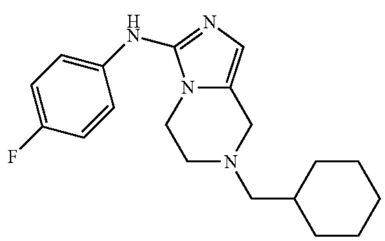 [SMILES: Fc1ccc(Nc2ncc3n2CCN(CC2CCCCC2)C3)cc1] | 7-(cyclohexylmethyl)-N-(4-fluorophenyl)-5,6,7,8-tetrahydroimidazo[1,5-a]pyrazin-3-amine | $^1$H NMR (CDCl$_3$) δ: 6.98-6.85 (m, 4H), 6.58 (s, 1H), 5.68 (s, 1H), 3.72 (t, J = 5.6 Hz, 2H), 3.58 (s, 2H), 2.75 (t, J = 5.6 Hz, 2H), 2.31 (d, J = 7.2 Hz, 2H), 1.88-1.62 (m, 5H), 1.61-1.43 (m, 1H), 1.32-1.10 (m, 3H), 0.90 (qd, J = 11.9, 3.1 Hz, 2H). |
| 9 | 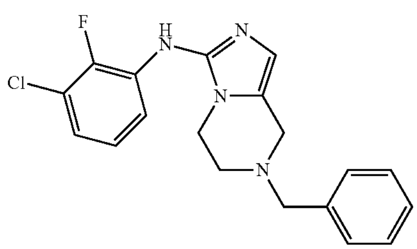 [SMILES: Fc1c(Cl)cccc1Nc1ncc2n1CCN(Cc1ccccc1)C2] | 7-benzyl-N-(3-chloro-2-fluorophenyl)-5,6,7,8-tetrahydroimidazo[1,5-a]pyrazin-3-amine | $^1$H NMR (CDCl$_3$) δ: 7.42-7.24 (m, 6H), 6.94 (td, J = 8.1, 1.5 Hz, 1H), 6.86 (ddd, J = 8.1, 6.5, 1.6 Hz, 1H), 6.61 (s, 1H), 5.93 (s, 1H), 3.80 (t, J = 5.6 Hz, 2H), 3.71 (s, 2H), 3.65 (s, 2H), 2.86 (t, J = 5.6 Hz, 2H). |
| 10 | 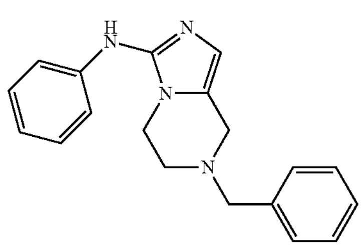 [SMILES: c1ccc(CN2CCn3c(cnc3Nc3ccccc3)C2)cc1] | 7-benzyl-N-phenyl-5,6,7,8-tetrahydroimidazo[1,5-a]pyrazin-3-amine | $^1$H NMR (CDCl$_3$) δ: 7.41-7.25 (m, 5H), 7.22 (dd, J = 8.6, 7.2 Hz, 2H), 6.94-6.82 (m, 3H), 6.60 (s, 1H), 5.76 (s, 1H), 3.74 (t, J = 5.6 Hz, 2H), 3.69 (s, 2H), 3.65 (s, 2H), 2.81 (t, J = 5.6 Hz, 2H). |
| 11 | 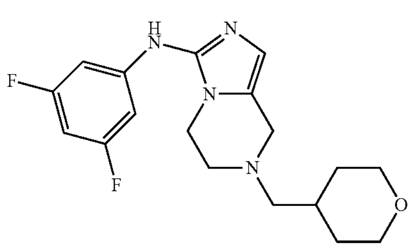 [SMILES: Fc1cc(F)cc(Nc2ncc3n2CCN(CC2CCOCC2)C3)c1] | N-(3,5-difluorophenyl)-7-((tetrahydro-2H-pyran-4-yl)methyl)-5,6,7,8-tetrahydroimidazo[1,5-a]pyrazin-3-amine | $^1$H NMR (CDCl$_3$) δ: 6.65 (s, 1H), 6.46-6.34 (m, 2H), 6.30 (tt, J = 9.1, 2.3 Hz, 1H), 6.04 (s, 1H), 3.98 (ddd, J = 11.3, 4.7, 1.7 Hz, 2H), 3.76 (t, J = 5.6 Hz, 2H), 3.62 (s, 2H), 3.40 (td, J = 11.8, 2.0 Hz, 3H), 2.80 (t, J = 5.6 Hz, 2H), 2.39 (d, J = 7.1 Hz, 2H), 1.90-1.74 (m, 1H), 1.76-1.64 (m, 2H), 1.37-1.26 (m, 2H). |

-continued

| EX | Structure | Name | NMR |
|---|---|---|---|
| 12 | 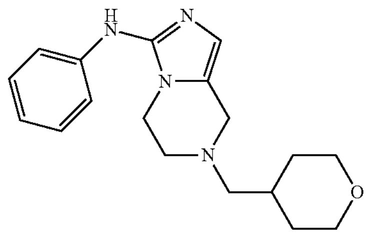 [SMILES: c1ccc(Nc2ncc3n2CCN(CC2CCOCC2)C3)cc1] | N-phenyl-7-((tetrahydro-2H-pyran-4-yl)methyl)-5,6,7,8-tetrahydroimidazo[1,5-a]pyrazin-3-amine | $^1$H NMR (CDCl$_3$) δ: 7.22 (dd, J = 8.8, 7.1 Hz, 2H), 6.93-6.80 (m, 3H), 6.63 (s, 1H), 5.76 (s, 1H), 3.98 (ddd, J = 11.6, 4.5, 1.8 Hz, 2H), 3.74 (t, J = 5.6 Hz, 2H), 3.62 (s, 2H), 3.40 (td, J = 11.8, 2.0 Hz, 2H), 2.77 (t, J = 5.6 Hz, 2H), 2.38 (d, J = 7.2 Hz, 2H), 1.88-1.74 (m, 1H), 1.74-1.64 (m, 2H), 1.39-1.21 (m, 2H). |
| 13 | 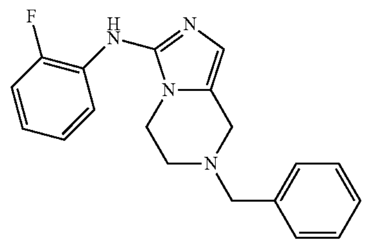 [SMILES: Fc1ccccc1Nc1ncc2n1CCN(Cc1ccccc1)C2] | 7-benzyl-N-(2-fluorophenyl)-5,6,7,8-tetrahydroimidazo[1,5-a]pyrazin-3-amine | $^1$H NMR (CDCl$_3$) δ: 7.46-7.26 (m, 6H), 7.09-6.97 (m, 2H), 6.87-6.75 (m, 1H), 6.60 (s, 1H), 5.80 (s, 1H), 3.80 (t, J = 5.7 Hz, 2H), 3.71 (s, 2H), 3.65 (s, 2H), 2.86 (t, J = 5.6 Hz, 2H). |
| 14 | 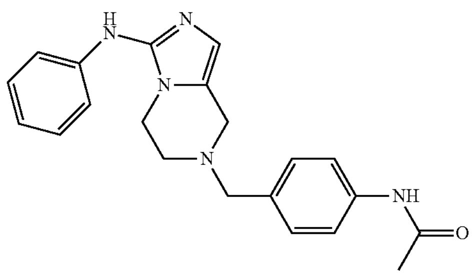 [SMILES: CC(=O)Nc1ccc(CN2CCn3c(cnc3Nc3ccccc3)C2)cc1] | N-(4-((3-(phenylamino)-5,6-dihydroimidazo[1,5-a]pyrazin-7(8H)-yl)methyl)phenyl)acetamide | $^1$H NMR (CDCl$_3$) δ: 7.47 (d, J = 8.1 Hz, 2H), 7.31 (d, J = 8.2 Hz, 2H), 7.23 (dd, J = 8.7, 7.3 Hz, 2H), 7.17 (s, 1H), 6.95-6.83 (m, 3H), 6.60 (s, 1H), 5.63 (s, 1H), 3.74 (t, J = 5.6 Hz, 2H), 3.65 (s, 2H), 3.63 (s, 2H), 2.80 (t, J = 5.6 Hz, 2H), 2.18 (s, 3H). |
| 15 | 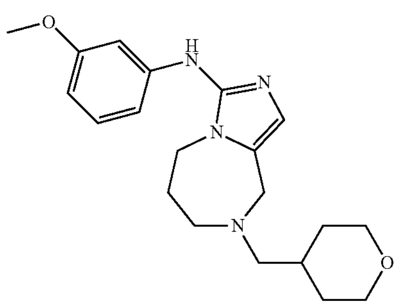 [SMILES: COc1cccc(Nc2ncc3n2CCCN(CC2CCOCC2)C3)c1] | N-(3-methoxyphenyl)-8-((tetrahydro-2H-pyran-4-yl)methyl)-6,7,8,9-tetrahydro-5H-imidazo[1,5-a][1,4]diazepin-3-amine | $^1$H NMR (CDCl$_3$) δ: 7.11 (t, J = 8.1 Hz, 1H), 6.75 (s, 1H), 6.43 (dd, J = 8.1, 2.3 Hz, 1H), 6.27 (dd, J = 7.9, 2.1 Hz, 1H), 6.23 (t, J = 2.3 Hz, 1H), 5.72 (s, 1H), 3.97 (dd, J = 11.4, 3.6 Hz, 2H), 3.94-3.87 (m, 2H), 3.78 (s, 2H), 3.75 (s, 3H), 3.39 (td, J = 11.8, 2.0 Hz, 2H), 3.10-3.03 (m, 2H), 2.26 (d, J = 7.0 Hz, 2H), 1.76-1.68 (m, 3H), 1.68-1.60 (m, 2H), 1.33-1.15 (m, 2H). |
| 16 | 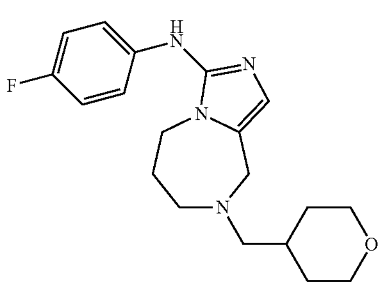 [SMILES: Fc1ccc(Nc2ncc3n2CCCN(CC2CCOCC2)C3)cc1] | N-(4-fluorophenyl)-8-((tetrahydro-2H-pyran-4-yl)methyl)-6,7,8,9-tetrahydro-5H-imidazo[1,5-a][1,4]diazepin-3-amine | $^1$H NMR (CDCl$_3$) δ: 6.92 (t, J = 8.7 Hz, 2H), 6.72 (s, 1H), 6.69 (dd, J = 8.9, 4.4 Hz, 2H), 5.68 (s, 1H), 3.97 (dd, J = 11.4, 3.5 Hz, 2H), 3.93-3.86 (m, 2H), 3.77 (s, 2H), 3.39 (td, J = 11.8, 1.9 Hz, 2H), 3.06 (t, J = 5.0 Hz, 2H), 2.26 (d, J = 6.9 Hz, 2H), 1.77-1.68 (m, 3H), 1.68-1.61 (m, 2H), 1.32-1.18 (m, 2H). |

-continued

| EX | Structure | Name | NMR |
|---|---|---|---|
| 17 | 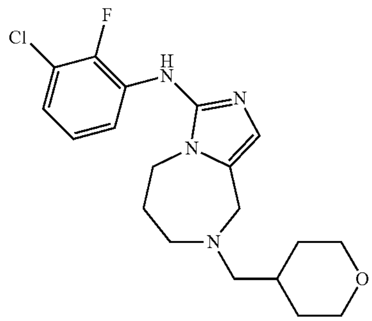 [SMILES: Fc1c(Cl)cccc1Nc1ncc2n1CCCN(CC1CCOCC1)C2] | N-(3-chloro-2-fluorophenyl)-8-((tetrahydro-2H-pyran-4-yl)methyl)-6,7,8,9-tetrahydro-5H-imidazo[1,5-a][1,4]diazepin-3-amine | $^1$H NMR (CDCl$_3$) δ: 6.96-6.81 (m, 2H), 6.79 (td, J = 7.5, 2.0 Hz, 1H), 6.76 (s, 1H), 5.86 (s, 1H), 4.07-3.90 (m, 4H), 3.78 (s, 2H), 3.39 (td, J = 11.8, 2.0 Hz, 2H), 3.12-3.02 (m, 2H), 2.25 (d, J = 6.9 Hz, 2H), 1.81-1.72 (m, 2H), 1.72-1.67 (m, 1H), 1.64-1.56 (m, 2H), 1.24 (qd, J = 12.8, 12.3, 4.4 Hz, 2H). |
| 18 | 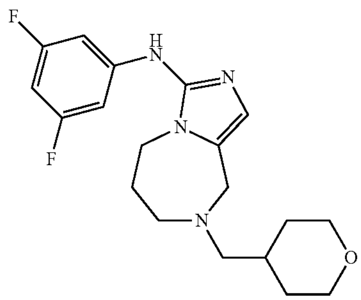 [SMILES: Fc1cc(F)cc(Nc2ncc3n2CCCN(CC2CCOCC2)C3)c1] | N-(3,5-difluorophenyl)-8-((tetrahydro-2H-pyran-4-yl)methyl)-6,7,8,9-tetrahydro-5H-imidazo[1,5-a][1,4]diazepin-3-amine | $^1$H NMR (CDCl$_3$) δ: 6.78 (s, 1H), 6.49 (s, 1H), 6.28 (tt, J = 9.0, 2.2 Hz, 1H), 6.23-6.11 (m, 2H), 3.97 (dd, J = 11.4, 3.5 Hz, 2H), 3.94-3.88 (m, 2H), 3.78 (s, 2H), 3.39 (td, J = 11.8, 2.0 Hz, 2H), 3.11-3.01 (m, 2H), 2.25 (d, J = 6.9 Hz, 2H), 1.79-1.67 (m, 3H), 1.67-1.60 (m, 2H), 1.34-1.17 (m, 2H). |
| 19 | 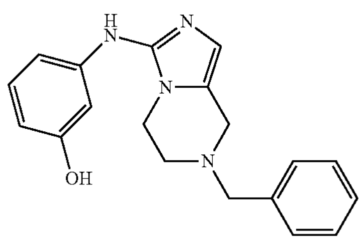 [SMILES: Oc1cccc(Nc2ncc3n2CCN(Cc2ccccc2)C3)c1] | 3-(7-benzyl-5,6,7,8-tetrahydroimidazo[1,5-a]pyrazin-3-ylamino)phenol | $^1$H NMR (DMSO) δ: 9.11 (s, 1H), 8.04 (s, 1H), 7.38-7.32 (m, 4H), 7.32-7.23 (m, 1H), 6.93 (t, J = 8.0 Hz, 1H), 6.87 (t, J = 2.1 Hz, 1H), 6.64 (dd, J = 8.1, 2.0 Hz, 1H), 6.38 (s, 1H), 6.16 (dd, J = 7.9, 2.3 Hz, 1H), 3.78 (t, J = 5.6 Hz, 2H), 3.66 (s, 2H), 3.49 (s, 2H), 2.80 (t, J = 5.6 Hz, 2H). |
| 20 | 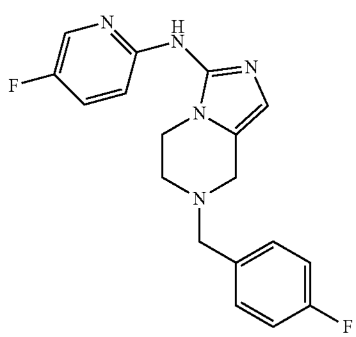 [SMILES: Fc1ccc(CN2CCn3c(cnc3Nc3ccc(F)cn3)C2)cc1] | 7-(4-fluorobenzyl)-N-(5-fluoropyridin-2-yl)-5,6,7,8-tetrahydroimidazo[1,5-a]pyrazin-3-amine | $^1$H NMR (CDCl$_3$) δ: 8.04-7.92 (m, 1H), 7.39-7.27 (m, 4H), 7.04 (t, J = 8.7 Hz, 2H), 6.49 (s, 1H), 3.83 (t, J = 5.7 Hz, 2H), 3.66 (s, 2H), 3.59 (s, 2H), 2.86 (t, J = 5.7 Hz, 2H). |
| 21 | 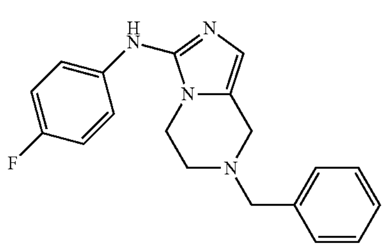 [SMILES: Fc1ccc(Nc2ncc3n2CCN(Cc2ccccc2)C3)cc1] | 7-benzyl-N-(4-fluorophenyl)-5,6,7,8-tetrahydroimidazo[1,5-a]pyrazin-3-amine | $^1$H NMR (CDCl$_3$) δ: 7.39-7.32 (m, 4H), 7.36-7.26 (m, 2H), 6.96-6.89 (m, 4H), 6.57 (s, 1H), 5.52 (s, 1H), 3.73 (t, J = 5.6 Hz, 2H), 3.70 (s, 2H), 3.65 (s, 2H), 2.82 (t, J = 5.6 Hz, 2H). |

| EX | Structure | Name | NMR |
|---|---|---|---|
| 22 | 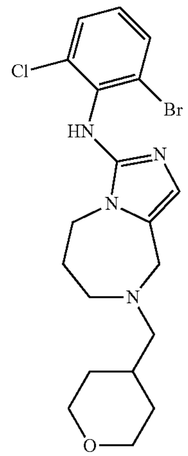 [SMILES: Clc1cccc(Br)c1Nc1ncc2n1CCCN(CC1CCOCC1)C2] | N-(2-bromo-6-chlorophenyl)-8-((tetrahydro-2H-pyran-4-yl)methyl)-6,7,8,9-tetrahydro-5H-imidazo[1,5-a][1,4]diazepin-3-amine | $^1$H NMR (CDCl$_3$) δ: 7.44 (dd, J = 8.1, 1.4 Hz, 1H), 7.30 (dd, J = 8.0, 1.4 Hz, 1H), 6.82 (t, J = 8.0 Hz, 1H), 6.66 (s, 1H), 5.77 (s, 1H), 4.24-4.08 (m, 2H), 3.96 (dd, J = 11.4, 3.4 Hz, 2H), 3.80 (s, 2H), 3.39 (td, J = 11.8, 2.0 Hz, 2H), 3.13 (t, J = 5.2 Hz, 2H), 2.26 (d, J = 6.9 Hz, 2H), 1.94-1.77 (m, 2H), 1.74-1.65 (m, 1H), 1.63-1.55 (m, 2H), 1.23 (qd, J = 13.0,12.3, 4.4 Hz, 2H). |

Example 23

N-(7-Benzyl-5,6,7,8-tetrahydroimidazo[1,5-a]pyrazin-3-yl)-N-phenylpropionamide

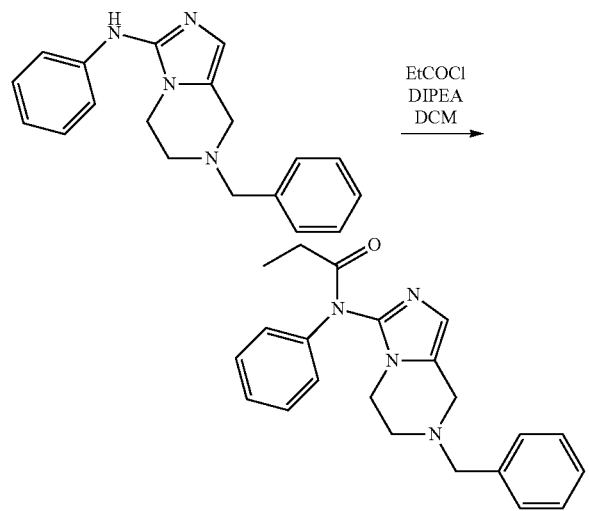

7-Benzyl-N-phenyl-5,6,7,8-tetrahydroimidazo[1,5-a]pyrazin-3-amine (61 mg, 0.20 mmol), described in example 10, was dissolved in dichloromethane (1 mL) and DIPEA (43 µl, 0.240 mmol) was added, followed by propionyl chloride (48 µl, 0.560 mmol added in three portions). After overnight stirring at room temperature, the reaction mixture was quenched with three drops of methanol and it was directly purified on silica-gel (gradient of 10% methanolic ethyl acetate in dichloromethane). Some other impurities and decomposition products were removed by preparative LC/MS. The title compound was obtained as a white solid (41 mg).

$^1$H NMR (CDCl$_3$) δ: 7.41-7.26 (m, 10H), 6.73 (s, 1H), 3.78-3.59 (m, 2H), 3.67 (s, 2H), 3.64 (s, 2H), 2.77 (t, J=5.6 Hz, 2H), 2.28 (q, J=7.4 Hz, 2H), 1.13 (t, J=7.4 Hz, 3H).

LC/MS m/z 361 [M+H]$^+$.

Examples 24-25 were prepared following the same method as in example 23, using the appropriate acyl chloride.

| EX | Structure | Name | NMR |
|---|---|---|---|
| 24 | 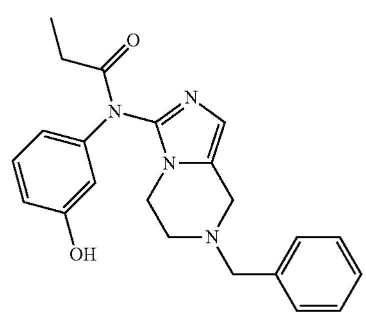 [SMILES: CCC(=O)N(c1cccc(O)c1)c1ncc2n1CCN(Cc1ccccc1)C2] | N-(7-benzyl-5,6,7,8-tetrahydroimidazo[1,5-a]pyrazin-3-yl)-N-(3-hydroxyphenyl)propionamide | $^1$H NMR (DMSO) δ: 8.43 (s, 1H), 7.41-7.30 (m, 4H), 7.34-7.23 (m, 2H), 7.24-7.12 (m, 2H), 6.50 (dt, J = 7.4, 1.8 Hz, 1H), 6.40 (s, 1H), 3.81 (t, J = 5.6, Hz 2H), 3.66 (s, 2H), 3.50 (s, 2H), 2.81 (t, J = 5.6 Hz, 2H), 2.58 (q, J = 7.5 Hz, 2H), 1.11 (t, J = 7.4 Hz, 3H). |

| EX | Structure | Name | NMR |
|---|---|---|---|
| 25 | 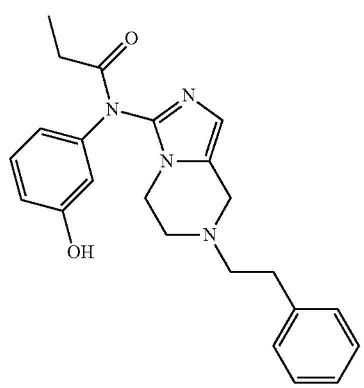 [SMILES: CCC(=O)N(c1cccc(O)c1)c1ncc2n1CCN(CCc1ccccc1)C2] | N-(3-hydroxyphenyl)-N-(7-phenethyl-5,6,7,8-tetrahydroimidazo[1,5-a]pyrazin-3-yl)propionamide | $^1$H NMR (CDCl$_3$) δ: 7.35-7.26 (m, 2H), 7.26-7.16 (m, 4H), 6.72 (ddd, J = 8.1, 2.2, 0.8 Hz, 1H), 6.67 (t, J = 2.2 Hz, 1H), 6.66 (t, J = 0.9 Hz, 1H), 6.60 (ddd, J = 8.1, 2.2, 0.9 Hz, 1H), 5.90 (s, 1H), 3.78 (t, J = 5.6 Hz, 2H), 3.74 (s, 2H), 2.93-2.84 (m, 4H), 2.84-2.73 (m, 2H), 2.55 (q, J = 7.6 Hz, 2H), 1.24 (t, J = 7.5 Hz, 3H). |

Example 26

7-Benzyl-N-methyl-N-phenyl-5,6,7,8-tetrahydroimidazo[1,5-a]pyrazin-3-amine

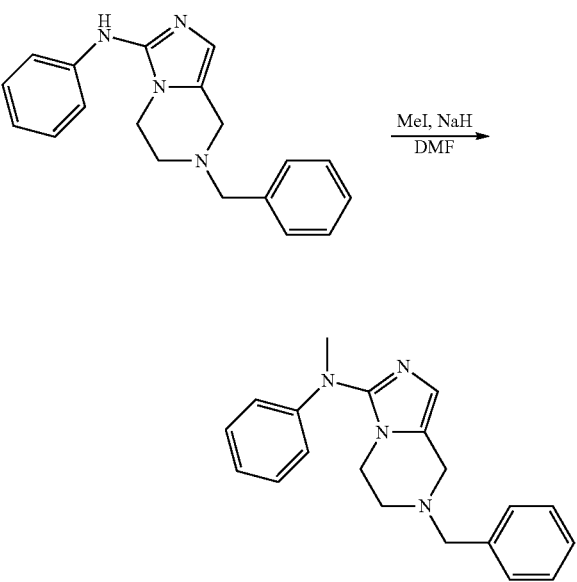

7-Benzyl-N-phenyl-5,6,7,8-tetrahydroimidazo[1,5-a]pyrazin-3-amine described in example 10 (150 mg, 0.493 mmol) was placed under a nitrogen atmosphere and dissolved in dimethylformamide (1.5 mL). Sodium hydride (22 mg of a 60% dispersion in oil, 0.550 mmol) was added, followed after 15 min, by iodomethane (37 μl, 0.591 mmol). After ~1 h of stirring the reaction mixture was concentrated and it was purified by flash column chromatography (gradient of methanol in DCM) to give the title compound as an oil (56 mg).

$^1$H NMR (CDCl$_3$) δ: 7.37-7.31 (m, 4H), 7.34-7.25 (m, 1H), 7.23 (dd, J=8.7, 7.3 Hz, 2H), 6.87 (tt, J=7.3, 1.1 Hz, 1H), 6.71-6.63 (m, 3H), 3.67 (s, 2H), 3.65 (s, 2H), 3.53 (t, J=5.6 Hz, 2H), 3.33 (s, 3H), 2.71 (t, J=5.6 Hz, 2H).

LC/MS m/z 319 [M+H]$^+$.

Example 27

N-Benzyl-7-(cyclohexylmethyl)-5,6,7,8-tetrahydroimidazo[1,5-a]pyrazin-3-amine

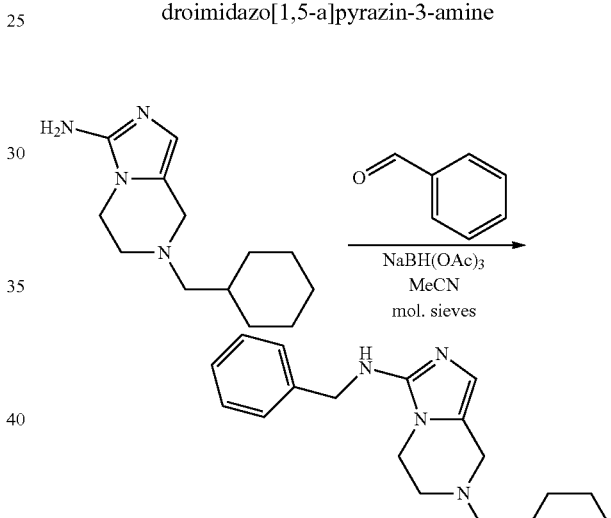

7-(Cyclohexylmethyl)-5,6,7,8-tetrahydroimidazo[1,5-a]pyrazin-3-amine (20 mg, 0.085 mmol), described in example 2.2, was dissolved in dry acetonitrile (1 mL). The solution was placed under nitrogen atmosphere and powdered molecular sieves (~100 mg, 3 Å) were added. Benzaldehyde (17 μl, 0.168 mmol) was then added and the reaction mixture was stirred for 4 h at reflux. The mixture was allowed to cool down to room temperature and sodium triacetoxyhydroborate (72 mg, 0.340 mmol) was added. After stirring overnight, the reaction mixture was quenched with water and then MeCN was driven off. 1M aqueous NaOH was added to pH ~14 followed by dichloromethane. After extraction, drying and solvent evaporation, the crude product was purified by preparative LC/MS to give the title compound (13.5 mg).

$^1$H NMR (CDCl$_3$) δ: 7.40 (d, J=7.5 Hz, 2H), 7.35 (t, J=7.3 Hz, 2H), 7.31-7.26 (m, 1H), 6.43 (s, 1H), 4.51 (d, J=5.9 Hz, 2H), 3.62 (t, J=5.6 Hz, 2H), 3.58-3.47 (m, 3H), 2.76 (t, J=5.6 Hz, 2H), 2.28 (d, J=7.2 Hz, 2H), 1.85-1.62 (m, 5H), 1.55-1.43 (m, 1H), 1.33-1.09 (m, 3H), 0.96-0.75 (m, 2H).

LC/MS m/z 325 [M+H]$^+$.

Example 28

3-Benzyl-7-(cyclohexylmethyl)-5,6,7,8-tetrahydroimidazo[1,5-a]pyrazine trifluoroacetate

28.1 (7-(Cyclohexylmethyl)-5,6,7,8-tetrahydroimidazo[1,5-a]pyrazin-3-yl)(phenyl)methanol

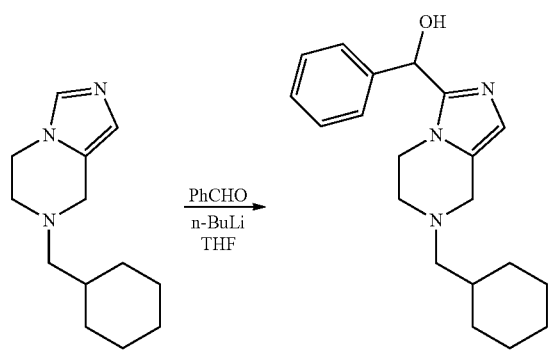 [SMILES: "PhCHO" ; c1ncn2c1CN(CC1CCCCC1)CC2 ; OC(c1ccccc1)c1ncc2n1CCN(CC1CCCCC1)C2]

7-(Cyclohexylmethyl)-5,6,7,8-tetrahydroimidazo[1,5-a]pyrazine (0.142 g, 0.50 mmol), described in preparation C, was dissolved in dry tetrahydrofuran (2 mL) under an atmosphere of nitrogen. The solution was cooled to −78° C. and was treated with n-butyllithium in hexanes (0.240 mL, 0.600 mmol). After stirring for 1 h, benzaldehyde (0.071 mL, 0.700 mmol) was added and the cooling bath removed. The mixture was allowed to warm up to room temperature overnight. Then it was quenched with aqueous ammonium chloride, diluted with water and extracted with ethyl acetate. The dried and concentrated extracts were purified on silica gel (gradient of 10% methanol/ethyl acetate mixture in dichloromethane) to give the title compound as a nearly colourless glass (138 mg).

$^1$H NMR (CDCl$_3$) δ 7.41-7.27 (m, 5H), 6.70 (s, 1H), 5.83 (s, 1H), 3.70 (dist. dt, J=11.5, 5.6 Hz, 1H), 3.59 (dist. dt, J=12.0, 5.6 Hz, 2H), 3.55 (s, 2H), 2.62 (t, J=5.6 Hz, 2H), 2.24 (d, J=7.2 Hz, 2H), 1.83-1.61 (m, 5H), 1.55-1.42 (m, 1H), 1.24-1.10 (m, 3H), 0.85 (dist q, J=~10.5 Hz, 2H).

LC/MS m/z 326 [M+H]$^+$.

28.2 3-Benzyl-7-(cyclohexylmethyl)-5,6,7,8-tetrahydroimidazo[1,5-a]pyrazine bis-trifluoroacetate

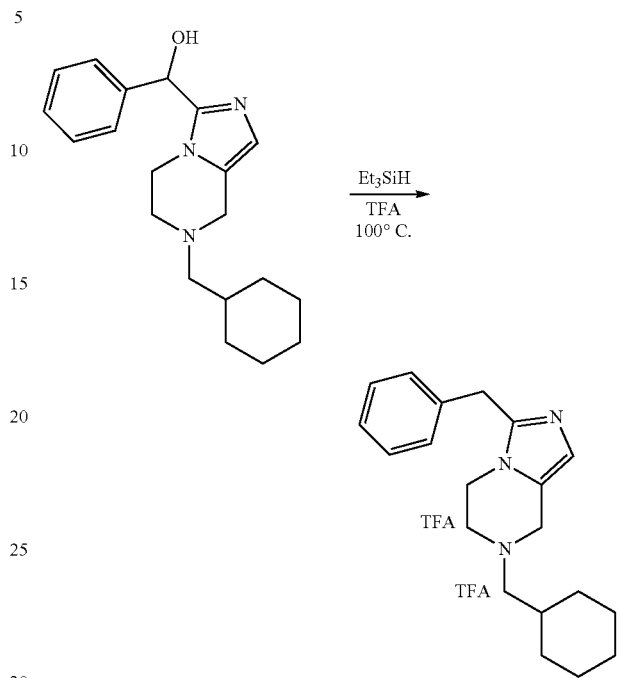

(7-(Cyclohexylmethyl)-5,6,7,8-tetrahydroimidazo[1,5-a]pyrazin-3-yl)(phenyl)methanol (0.138 g, 0.42 mmol) was treated with a mixture of triethylsilane (1.017 mL, 6.30 mmol) and 2,2,2-trifluoroacetic acid (0.468 mL, 6.30 mmol) at 100° C. for ~20 h. The mixture was then concentrated and purified by flash column to give the title compound as a colourless oil (194 mg).

$^1$H NMR (CDCl$_3$) δ: 7.38-7.27 (m, 3H), 7.17 (d, J=7.4 Hz, 2H), 7.08 (s, 1H), 4.38 (s, 2H), 3.91 (t, J=5.3 Hz, 2H), 3.80 (s, 2H), 3.05-2.92 (m, 2H), 2.47 (d, J=6.9 Hz, 2H), 1.83-1.61 (m, 5H), 1.61-1.43 (m, 1H), 1.34-1.08 (m, 3H), 1.01-0.75 (m, 2H).

LC/MS m/z 310 [M+H]$^+$.

Examples 29-30 were prepared following the same method as in example 28, using the appropriate aldehyde.

| EX | Structure | Name | NMR |
|---|---|---|---|
| 29 | (4-fluorobenzyl / tetrahydropyran structure) | 3-(4-fluorobenzyl)-7-((tetrahydro-2H-pyran-4-yl)methyl)-5,6,7,8-tetrahydroimidazo[1,5-a]pyrazine hydrochloride | $^1$H NMR (DMSO) δ: 11.82 (s, 1H), 7.56 (s, 1H), 7.40 (dd, J = 8.5, 5.5 Hz, 2H), 7.22 (t, J = 8.8 Hz, 2H), 4.45 (s, 2H), 4.51-4.26 (m, 2H), 4.06-3.77 (m, 6H), 3.84 (dd, J = 11.6, 2.9 Hz, 2H), 3.29 (td, J = 11.7, 2.0 Hz, 2H), 2.17-1.97 (m, 1H), 1.84-1.64 (m, 2H), 1.34-1.14 (m, 2H). |

| EX | Structure | Name | NMR |
|---|---|---|---|
| 30 | (structure shown) ·HCl | 7-(cyclohexylmethyl)-3-(4-fluorobenzyl)-5,6,7,8-tetrahydroimidazo[1,5-a]pyrazine hydrocloride | 1H NMR (DMSO) δ: 11.63 (s, 1H), 7.56 (s, 1H), 7.41 (dd, J = 8.5, 5.4 Hz, 2H), 7.22 (t, J = 8.8 Hz, 2H), 4.84-4.20 (m, 6H), 3.78-3.34 (m, 2H), 3.21-2.90 (m, 2H), 1.97-1.73 (m, 3H), 1.76-1.54 (m, 3H), 1.33-1.04 (m, 3H), 1.05-0.82 (m, 2H). |

Example 31

7-Phenethyl-N-phenyl-5,6,7,8-tetrahydroimidazo[1,5-a]pyrazin-3-amine

31.1 N-Phenyl-5,6,7,8-tetrahydroimidazo[1,5-a]pyrazin-3-amine

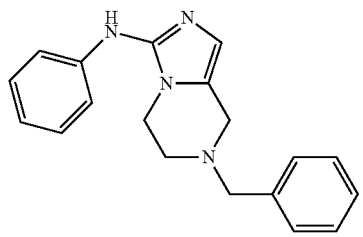

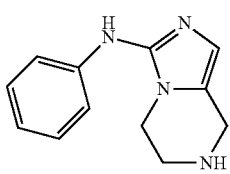

7-Benzyl-N-phenyl-5,6,7,8-tetrahydroimidazo[1,5-a]pyrazin-3-amine (0.457 g, 1.5 mmol) described in example 10 was dissolved in a mixture of ethyl acetate (10 mL) and methanol (10 mL). 10% palladium on carbon (600 mg) was added in several portions to the solution stirring first at room temperature, then at 50° C. till the completion of reaction as monitored by TLC. The reaction mixture was then filtered through celite, the filtration cake rinsed with ethyl acetate and methanol and the filtrate evaporated to dryness. Flash column on silica (gradient of 7 N methanolic ammonia in dichloromethane) provided the title compound as white foam (159 mg).

$^1$H NMR (CDCl$_3$) δ 7.25-7.19 (m, 2H), 6.91-6.85 (m, 3H), 6.64 (s, 1H), 5.85 (br s, 1H), 4.05 (d, J=0.8 Hz, 2H), 3.68 (t, J=5.6 Hz, 2H), 3.17 (t, J=5.6 Hz, 2H), 1.64 (br s, 1H).

LC/MS m/z 215 [M+H]$^+$.

31.2 7-Phenethyl-N-phenyl-5,6,7,8-tetrahydroimidazo[1,5-a]pyrazin-3-amine

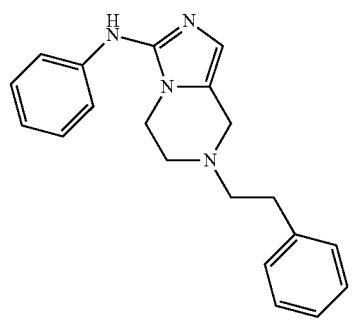

N-Phenyl-5,6,7,8-tetrahydroimidazo[1,5-a]pyrazin-3-amine (0.053 g, 0.24 mmol) was dissolved in absolute ethanol (2 mL) and 2-phenylacetaldehyde (0.037 mL, 0.288 mmol) was added and the mixture was stirred for 1 h. Then, sodium triacetoxyhydroborate (0.153 g, 0.720 mmol) was added and stirring was continued for 1 h more. The mixture was then diluted with DCM, filtered through celite and concentrated to dryness. Flash chromatography on silica (gradient of methanol in dichloromethane) provided the title compound as a yellow glass (58 mg).

$^1$H NMR (CDCl$_3$) δ: 7.36-7.26 (m, 2H), 7.27-7.18 (m, 5H), 6.93-6.84 (m, 3H), 6.65 (s, 1H), 5.69 (s, 1H), 3.77 (t, J=5.6 Hz, 2H), 3.74 (s, 2H), 2.93-2.83 (m, 4H), 2.85-2.75 (m, 2H).

LC/MS m/z 319 [M+H]$^+$.

Examples 32-40 were prepared following the same method as in example 31, using the appropriate aldehyde or ketone.

| EX | Structure | Name | NMR |
|---|---|---|---|
| 32 | 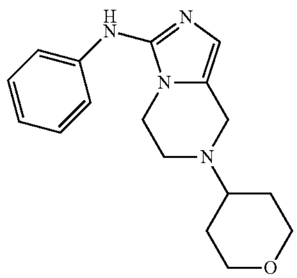 [SMILES: c1ccc(Nc2ncc3n2CCN(C2CCOCC2)C3)cc1] | N-phenyl-7-(tetrahydro-2H-pyran-4-yl)-5,6,7,8-tetrahydroimidazo[1,5-a]pyrazin-3-amine | $^1$H NMR (CDCl$_3$) δ: 7.22 (t, J = 7.9 Hz, 2H), 6.95-6.82 (m, 3H), 6.65 (s, 1H), 5.77 (s, 1H), 4.06 (dd, J = 11.2, 3.9 Hz, 2H), 3.79 (s, 2H), 3.74 (t, J = 5.6 Hz, 2H), 3.41 (td, J = 11.9, 2.0 Hz, 2H), 2.91 (t, J = 5.6 Hz, 2H), 2.65 (tt, J = 11.3, 3.9 Hz, 1H), 1.92-1.76 (m, 2H), 1.64 (qd, J = 12.1, 4.4 Hz, 2H). |
| 33 | 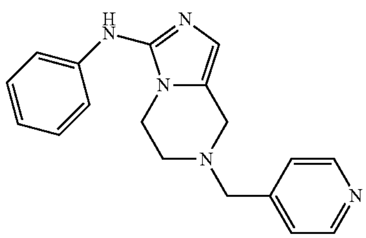 [SMILES: c1ccc(Nc2ncc3n2CCN(Cc2ccncc2)C3)cc1] | N-phenyl-7-(pyridin-4-ylmethyl)-5,6,7,8-tetrahydroimidazo[1,5-a]pyrazin-3-amine | $^1$H NMR (CDCl$_3$) δ: 8.58 (d, J = 6.0 Hz, 2H), 7.32 (d, J = 5.9 Hz, 2H), 7.26-7.20 (m, 2H), 6.94-6.84 (m, 3H), 6.62 (s, 1H), 5.66 (s, 1H), 3.77 (t, J = 5.6 Hz, 2H), 3.71 (s, 2H), 3.67 (s, 2H), 2.83 (t, J = 5.6 Hz, 2H). |
| 34 | 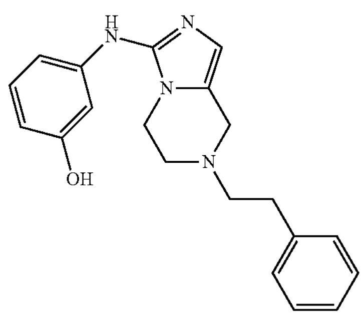 [SMILES: Oc1cccc(Nc2ncc3n2CCN(CCc2ccccc2)C3)c1] | 3-(7-phenethyl-5,6,7,8-tetrahydroimidazo[1,5-a]pyrazin-3-ylamino)phenol | $^1$H NMR (DMSO) δ: 9.11 (s, 1H), 8.04 (s, 1H), 7.34-7.21 (m, 4H), 7.18 (td, J = 6.6, 2.7 Hz, 1H), 6.93 (t, J = 8.0 Hz, 1H), 6.87 (t, J = 2.3 Hz, 1H), 6.64 (dd, J = 7.9, 2.1 Hz, 1H), 6.41 (s, 1H), 6.16 (dd, J = 7.9, 2.2 Hz, 1H), 3.76 (t, J = 5.6 Hz, 2H), 3.60 (s, 2H), 2.89-2.76 (m, 4H), 2.69 (dd, J = 9.2, 6.2 Hz, 2H). |
| 35 | 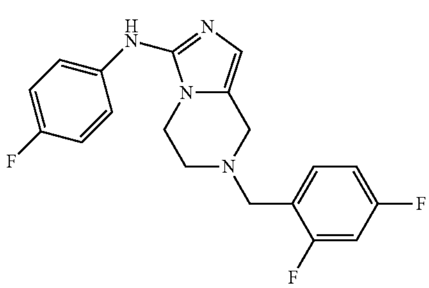 [SMILES: Fc1ccc(Nc2ncc3n2CCN(Cc2ccc(F)cc2F)C3)cc1] | 7-(2,4-difluorobenzyl)-N-(4-fluorophenyl)-5,6,7,8-tetrahydroimidazo[1,5-a]pyrazin-3-amine | $^1$H NMR (CDCl$_3$) δ: 7.39 (td, J = 8.4, 6.5 Hz, 1H), 6.98-6.78 (m, 6H), 6.59 (s, 1H), 5.61 (s, 1H), 3.74 (t, J = 5.6 Hz, 2H), 3.72 (s, 2H), 3.66 (s, 2H), 2.85 (t, J = 5.6 Hz, 2H). |
| 36 | 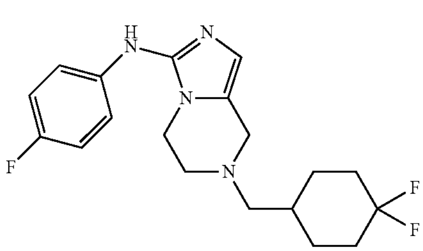 [SMILES: Fc1ccc(Nc2ncc3n2CCN(CC2CCC(F)(F)CC2)C3)cc1] | 7-((4,4-difluorocyclohexyl)methyl)-N-(4-fluorophenyl)-5,6,7,8-tetrahydroimidazo[1,5-a]pyrazin-3-amine | $^1$H NMR (CDCl$_3$) δ: 6.99-6.86 (m, 4H), 6.60 (s, 1H), 5.61 (s, 1H), 3.73 (t, J = 5.6 Hz, 2H), 3.61 (s, 2H), 2.78 (t, J = 5.6 Hz, 2H), 2.38 (d, J = 7.3 Hz, 2H), 2.20-2.01 (m, 2H), 1.96-1.84 (m, 2H), 1.82-1.60 (m, 3H), 1.35-1.17 (m, 2H). |

| EX | Structure | Name | NMR |
|----|-----------|------|-----|
| 37 | 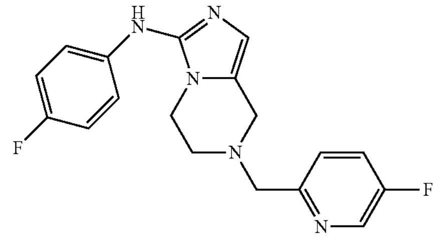 [SMILES: Fc1ccc(Nc2ncc3n2CCN(Cc2ccc(F)cn2)C3)cc1] | N-(4-fluorophenyl)-7-((5-fluoropyridin-2-yl)methyl)-5,6,7,8-tetrahydroimidazo[1,5-a]pyrazin-3-amine | $^1$H NMR (CDCl$_3$) δ: 8.44 (d, J = 2.8 Hz, 1H), 7.46 (dd, J = 8.6, 4.6 Hz, 1H), 7.41 (td, J = 8.3, 2.8 Hz, 1H), 6.98-6.86 (m, 4H), 6.58 (s, 1H), 5.62 (s, 1H), 3.84 (s, 2H), 3.76 (t, J = 5.6 Hz, 2H), 3.70 (s, 2H), 2.89 (t, J = 5.6 Hz, 2H). |
| 38 | 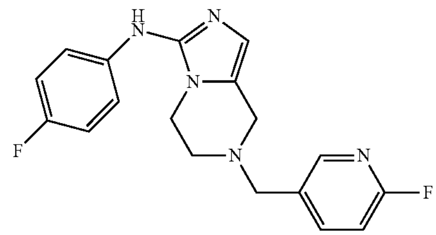 [SMILES: Fc1ccc(Nc2ncc3n2CCN(Cc2ccc(F)nc2)C3)cc1] | N-(4-fluorophenyl)-7-((6-fluoropyridin-3-yl)methyl)-5,6,7,8-tetrahydroimidazo[1,5-a]pyrazin-3-amine | $^1$H NMR (CDCl$_3$) δ: 8.17 (d, J = 2.4 Hz, 1H), 7.84 (td, J = 8.1, 2.5 Hz, 1H), 6.99-6.87 (m, 5H), 6.59 (s, 1H), 5.67 (s, 1H), 3.73 (t, J = 5.6 Hz, 2H), 3.69 (s, 2H), 3.64 (s, 2H), 2.83 (t, J = 5.6 Hz, 2H). |
| 39 | 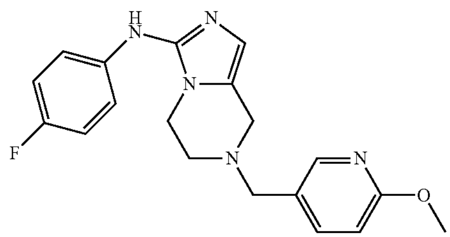 [SMILES: COc1ccc(CN2CCn3c(cnc3Nc3ccc(F)cc3)C2)cn1] | N-(4-fluorophenyl)-7-((6-methoxypyridin-3-yl)methyl)-5,6,7,8-tetrahydroimidazo[1,5-a]pyrazin-3-amine | $^1$H NMR (CDCl$_3$) δ: 8.08 (d, J = 2.4 Hz, 1H), 7.61 (dd, J = 8.5, 2.4 Hz, 1H), 6.98-6.86 (m, 4H), 6.75 (d, J = 8.5 Hz, 1H), 6.58 (s, 1H), 5.60 (s, 1H), 3.94 (s, 3H), 3.71 (t, J = 5.6 Hz, 2H), 3.63 (s, 2H), 3.61 (s, 2H), 2.81 (t, J = 5.6 Hz, 2H). |
| 40 | 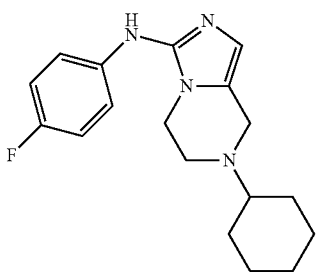 [SMILES: Fc1ccc(Nc2ncc3n2CCN(C2CCCCC2)C3)cc1] | 7-cyclohexyl-N-(4-fluorophenyl)-5,6,7,8-tetrahydroimidazo[1,5-a]pyrazin-3-amine | $^1$H NMR (CDCl$_3$) δ: 6.97-6.84 (m, 4H), 6.59 (s, 1H), 5.65 (s, 1H), 3.78 (s, 2H), 3.71 (t, J = 5.5 Hz, 2H), 2.91 (t, J = 5.6 Hz, 2H), 2.53-2.40 (m, 1H), 1.98-1.77 (m, 4H), 1.34-1.20 (m, 5H), 1.20-1.06 (m, 1H). |

Example 41

7-(3-Methoxyphenethyl)-N-phenyl-5,6,7,8-tetrahydroimidazo[1,5-a]pyrazin-3-amine

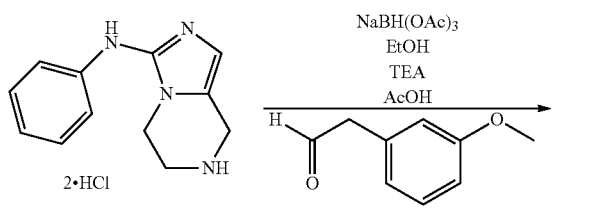

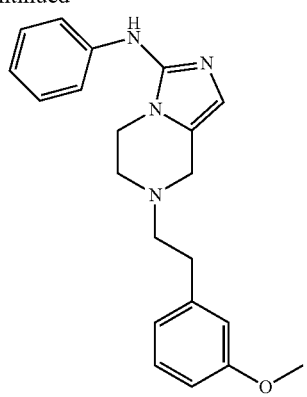

N-Phenyl-5,6,7,8-tetrahydroimidazo[1,5-a]pyrazin-3-amine dihydrochloride (150 mg, 0.52 mmol, prepared from example 31.1 using HCl in ethanol) was suspended in absolute ethanol (10 mL) under a nitrogen atmosphere. Triethylamine (146 μl, 1.04 mmol) was added followed by 2-(3-methoxyphenyl)acetaldehyde (1.40 mmol) and a drop of AcOH. The mixture was stirred for 2 h at room temperature, then sodium triacetoxyborohydride (332 mg, 1.567 mmol) was added and the suspension was stirred at room temperature overnight. After quenching with water, ethanol was driven off and the residue was diluted with dichloromethane and aqueous sodium bicarbonate. The crude product obtained after extraction, drying, filtration and solvent evaporation was purified by flash chromatography (gradient of methanol in dichloromethane) and preparative LC/MS to give the title compound as a white solid (81 mg).

LC/MS m/z 349 [M+H]+.

Examples 42-44 were prepared following the same method as in example 47, using the appropriate aldehyde.

| EX | Structure | Name | NMR |
|----|-----------|------|-----|
| 42 | 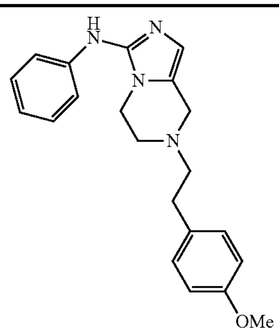 | 7-(4-methoxyphenethyl)-N-phenyl-5,6,7,8-tetrahydroimidazo[1,5-a]pyrazin-3-amine | |
| 43 | 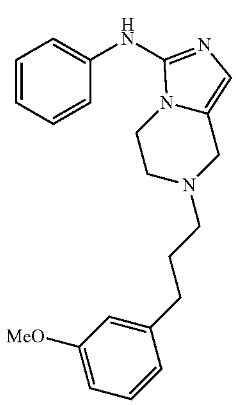 [SMILES: COc1cccc(CCCN2CCn3c(cnc3Nc3ccccc3)C2)c1] | 7-(3-(3-methoxyphenyl)propyl)-N-phenyl-5,6,7,8-tetrahydroimidazo[1,5-a]pyrazin-3-amine | |
| 44 | 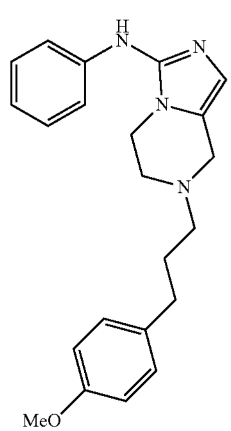 [SMILES: COc1ccc(CCCN2CCn3c(cnc3Nc3ccccc3)C2)cc1] | 7-(3-(4-methoxyphenyl)propyl)-N-phenyl-5,6,7,8-tetrahydroimidazo[1,5-a]pyrazin-3-amine | |

Example 45

3-(2-(3-(Phenylamino)-5,6-dihydroimidazo[1,5-a]pyrazin-7(8H)-yl)ethyl)phenol

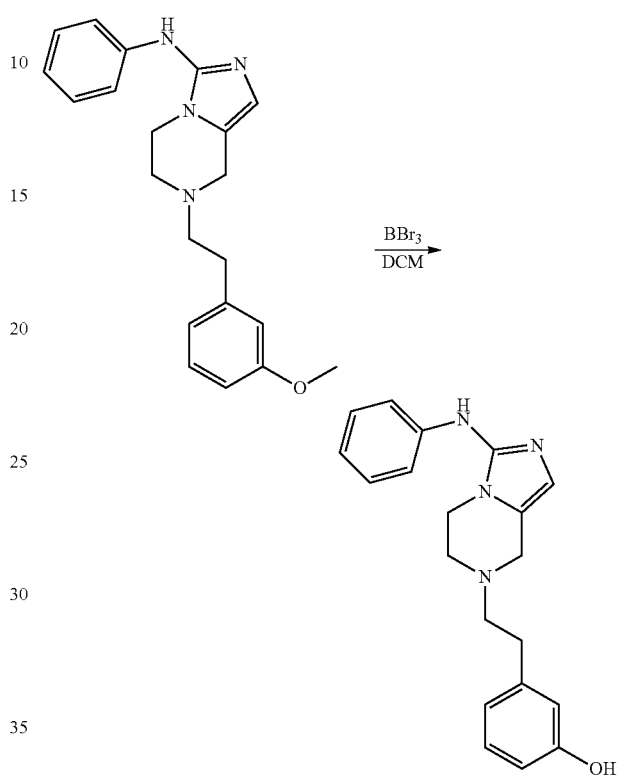

7-(3-Methoxyphenethyl)-N-phenyl-5,6,7,8-tetrahydroimidazo[1,5-a]pyrazin-3-amine (0.80 g, 0.23 mmol), described in example 47, was dissolved in dichloromethane (10 mL). The solution was cooled to −78° C. and it was treated with an excess of tribromoborane (0.766 mL, 1.532 mmol). The reaction mixture as a white suspension was allowed to warm up to room temperature. Then the mixture was quenched with water and methanol and extracted with dichloromethane from aqueous sodium bicarbonate. The crude product was first purified using flash chormatography on silica gel (gradient of 7N methanolic ammonia in ethyl acetate) and then purified further by means of preparative TLC. The title compound was obtained as a white solid after freeze-drying from acetonitrile (58 mg).

$^1$H NMR (DMSO) δ: 9.26 (s, 1H), 8.19 (s, 1H), 7.35 (d, J=8.0 Hz, 2H), 7.17 (t, J=7.8 Hz, 2H), 7.06 (t, J=7.7 Hz, 1H), 6.76 (t, J=7.3 Hz, 1H), 6.66 (d, J=8.0 Hz, 1H), 6.64 (d, J=2.1 Hz, 1H), 6.58 (dd, J=7.9, 2.3 Hz, 1H), 6.41 (s, 1H), 3.78 (t, J=5.6 Hz, 2H), 3.59 (s, 2H), 2.84 (t, J=5.6 Hz, 2H), 2.77-2.69 (m, 2H), 2.69-2.62 (m, 2H).

LC/MS m/z 335 [M+H]+, m/z 333 [M−H]−.

Examples 46-48 were prepared following the same method as in example 51, starting from the corresponding examples 48 to 50.

| EX | Structure | Name | NMR |
|----|-----------|------|-----|
| 46 | 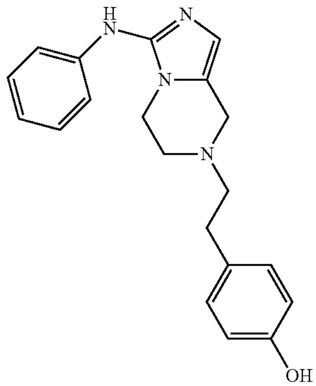 [SMILES: Oc1ccc(CCN2CCn3c(cnc3Nc3ccccc3)C2)cc1] | 4-(2-(3-(phenylamino)-5,6-dihydroimidazo[1,5-a]pyrazin-7(8H)-yl)ethyl)phenol | $^1$H NMR (DMSO) δ: 9.16 (s, 1H), 8.18 (s, 1H), 7.34 (d, J = 7.9 Hz, 2H), 7.17 (t, J = 7.8 Hz, 2H), 7.03 (d, J = 8.4 Hz, 2H), 6.76 (t, J = 7.3 Hz, 1H), 6.66 (d, J = 8.4 Hz, 2H), 6.41 (s, 1H), 3.77 (t, J = 5.6 Hz, 2H), 3.58 (s, 2H), 2.83 (t, J = 5.6 Hz, 2H), 2.74-2.65 (m, 2H), 2.65-2.58 (m, 2H). |
| 47 | 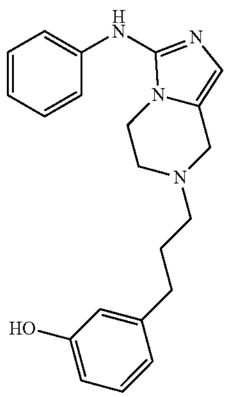 [SMILES: Oc1cccc(CCCN2CCn3c(cnc3Nc3ccccc3)C2)c1] | 3-(3-(3-(phenylamino)-5,6-dihydroimidazo[1,5-a]pyrazin-7(8H)-yl)propyl)phenol | $^1$H NMR (DMSO) δ: 9.24 (s, 1H), 8.18 (s, 1H), 7.34 (d, J = 7.8 Hz, 2H), 7.17 (dd, J = 8.5, 7.2 Hz, 2H), 7.05 (t, J = 7.7 Hz, 1H), 6.75 (t, J = 7.2 Hz, 1H), 6.62 (d, J = 7.6 Hz, 1H), 6.60 (d, J = 2.1 Hz, 1H), 6.56 (dd, J = 7.8, 2.0 Hz, 1H), 6.41 (s, 1H), 3.78 (t, J = 5.6 Hz, 2H), 3.51 (s, 2H), 2.76 (t, J = 5.6 Hz, 2H), 2.53 (t, J = 7.7 Hz, 2H), 2.45 (t, J = 7.3 Hz, 2H), 1.76 (p, J = 7.5 Hz, 2H). |
| 48 | 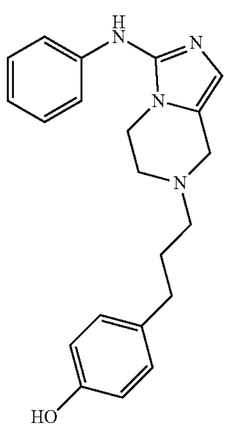 [SMILES: Oc1ccc(CCCN2CCn3c(cnc3Nc3ccccc3)C2)cc1] | 4-(3-(3-(phenylamino)-5,6-dihydroimidazo[1,5-a]pyrazin-7(8H)-yl)propyl)phenol | $^1$H NMR (DMSO) δ: 9.13 (s, 1H), 8.18 (s, 1H), 7.34 (d, J = 8.0 Hz, 2H), 7.17 (t, J = 7.9 Hz, 2H), 6.99 (d, J = 8.4 Hz, 2H), 6.75 (t, J = 7.3 Hz, 1H), 6.66 (d, J = 8.4 Hz, 2H), 6.40 (s, 1H), 3.77 (t, J = 5.7 Hz, 2H), 3.50 (s, 2H), 2.75 (t, J = 5.6 Hz, 2H), 2.51-2.47 (m, 2H), 2.43 (t, J = 7.2 Hz, 2H), 1.73 (p, J = 7.5 Hz, 2H). |

Biological Activity

Pharmacological Study

Brain membrane preparation and binding assays for the $\sigma_1$-receptor were performed as described (DeHaven-Hudkins, D. L., L. C. Fleissner, and F. Y. Ford-Rice, 1992, Characterization of the binding of [$^3$H](+)pentazocine to σ recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was re-suspended in fresh Tris-HCl buffer (50 mM, pH 7.4) and stored on ice until use.

The radioligand used was [$^3$H]-(+)-pentazocine at 5.0 nM and the final volume was 200 μl. The incubation was initiated with the addition of 100 μl of membrane at a final tissue concentration of approximately 5 mg tissue net weight/mL and the incubation time was 150 m. at 37° C. After incubation, the membranes were collected onto pre-treated glass fiber filterplate (MultiScreen-FC, Millipore), with polyethylenimine 0.1%. The filters were washed two times with 200 μl of washing buffer (50 mM Tris Cl, pH=7.4) and then 25 μl of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

Some of the results obtained are shown in table (I).

TABLE (I)

| EX | $K_i$ (nM) |
|---|---|
| 1 | 179 |
| 2 | 106 |
| 3 | 71 |
| 5 | 8.2 |
| 6 | 12 |
| 7 | 13 |
| 8 | 8 |
| 9 | 232 |
| 10 | 58 |
| 12 | 258 |
| 15 | 266 |
| 16 | 175 |
| 17 | 14 |
| 18 | 26 |
| 19 | 63 |
| 20 | 67 |
| 21 | 44 |
| 24 | 124 |
| 25 | 358 |
| 27 | 38 |
| 28 | 39 |
| 30 | 22 |
| 31 | 101 |
| 34 | 168 |
| 35 | 37 |
| 36 | 21 |
| 37 | 293 |
| 38 | 311 |
| 39 | 373 |
| 40 | 68 |

The invention claimed is:
1. A compound of formula (I):

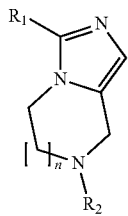

wherein
$R_1$ is selected from the group consisting of —NR$_4$COR$_3$, —NHCONHR$_3$, —(C(R$_{51}$R$_{52}$))$_m$—R$_6$, and —NR$_{71}$R$_{72}$;
$R_2$ is selected from the group consisting of —(C(R$_{81}$R$_{82}$))$_p$—R$_9$, a substituted or unsubstituted cycloalkyl group, and a substituted or unsubstituted heterocycloalkyl group;
$R_3$ is selected from the group consisting of a linear or branched, substituted or unsubstituted $C_{1-10}$alkyl group, a linear or branched, substituted or unsubstituted $C_{2-10}$alkenyl group, a linear or branched, substituted or unsubstituted $C_{2-10}$alkynyl group, a substituted or unsubstituted cycloalkyl group, a substituted or unsubstituted cycloalkylalkyl group, a substituted or unsubstituted heterocycloalkyl group, and a substituted or unsubstituted heterocycloalkylalkyl group;
$R_4$, is selected from the group consisting of a hydrogen atom, a linear or branched, substituted or unsubstituted $C_{1-10}$alkyl group, a linear or branched, substituted or unsubstituted $C_{2-10}$alkenyl group, a linear or branched, substituted or unsubstituted $C_{2-10}$alkynyl group, a substituted or unsubstituted cycloalkyl group, a substituted or unsubstituted cycloalkylalkyl group, a substituted or unsubstituted aryl group, a substituted or unsubstituted arylalkyl group, a substituted or unsubstituted heterocycloalkyl group, a substituted or unsubstituted heterocycloalkylalkyl group, a substituted or unsubstituted heteroaryl group, and a substituted or unsubstituted heteroarylalkyl group;
$R_{51}$, $R_{52}$, $R_{81}$ and $R_{82}$ are selected independently from the group consisting of a hydrogen atom, a linear or branched, substituted or unsubstituted $C_{1-3}$alkyl group, a linear or branched, substituted or unsubstituted $C_{2-3}$alkenyl group, and a linear or branched, substituted or unsubstituted $C_{2-3}$alkynyl group;
$R_6$ is selected from the group consisting of a substituted or unsubstituted aryl group, and a substituted or unsubstituted heteroaryl group;
$R_{71}$ is selected from the group consisting of a substituted or unsubstituted cycloalkyl group, a substituted or unsubstituted cycloalkylalkyl group, a substituted or unsubstituted aryl group, a substituted or unsubstituted arylalkyl group, a substituted or unsubstituted heterocycloalkyl group, a substituted or unsubstituted heterocycloalkylalkyl group, a substituted or unsubstituted heteroaryl group, and a substituted or unsubstituted heteroarylalkyl group;
$R_{72}$ is selected from the group consisting of a hydrogen atom, a linear or branched, substituted or unsubstituted $C_{1-3}$alkyl group, a linear or branched, substituted or unsubstituted $C_{2-3}$alkenyl group, and a linear or branched, substituted or unsubstituted $C_{2-3}$alkynyl group;
$R_9$ is selected from the group consisting of a substituted or unsubstituted cycloalkyl group, a substituted or unsubstituted aryl group, a substituted or unsubstituted heterocycloalkyl group, and a substituted or unsubstituted heteroaryl group;
n is 1, 2, or 3;
m is 1, 2, or 3;
p is 1, 2, or 3;
wherein the $C_{1-10}$alkyl group, the $C_{2-10}$alkenyl group, the $C_{2-10}$alkynyl group, the cycloalkyl group, the heterocycloalkyl group, the aryl group and the heteroaryl group as defined in formula (I), if substituted, are substituted by one or more substituents selected from the group consisting of a $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —SO$_2$R', —NHR', —NR'R" wherein R' and R" for each substituent independently represents a linear or branched $C_{1-6}$-alkyl radical;
optionally as a stereoisomer, including enantiomers and diastereomers, a racemate or a mixture of at least two of the stereoisomers, including enantiomers and diastereomers, in any mixing ratio, or a pharmaceutically acceptable salt, or solvate thereof.
2. The compound according to claim 1, wherein $R_1$ represents —NR$_{71}$R$_{72}$.
3. The compound according to claim 1, wherein $R_1$ represents —NR$_{71}$R$_{72}$, wherein $R_{71}$ is a substituted or unsubstituted aryl group and $R_{72}$ is a hydrogen atom.
4. The compound according to claim 1, wherein $R_1$ represents —(C(R$_{51}$R$_{52}$))$_m$—R$_6$.

5. The compound according to claim 1, wherein $R_1$ represents a group $—(C(R_{51}R_{52}))_m—R_6$ in which $R_6$ is a substituted or unsubstituted aryl group.

6. The compound according to claim 1, wherein $R_1$ is selected from the group consisting of $—NR_4COR_3$, and $—NHCONHR_3$.

7. The compound according to claim 1, wherein $R_2$ is a $—(C(R_{81}R_{82}))_p—R_9$ group in which $R_{81}$ and $R_{82}$ each represent a hydrogen atom.

8. The compound according to claim 1, wherein, taken together or separately, n is 1 or 2, m is 1, and p is 1.

9. The compound according to claim 1, which is selected from the group consisting of:
   1-(8-(cyclohexylmethyl)-6,7,8,9-tetrahydro-5H-imidazo [1,5-a][1,4]diazepin-3-yl)-3-ethylurea,
   1-(7-(cyclohexylmethyl)-5,6,7,8-tetrahydroimidazo[1,5-a]pyrazin-3-yl)-3-ethylurea,
   1-(7-(cyclohexylmethyl)-5,6,7,8-tetrahydroimidazo[1,5-a]pyrazin-3-yl)-3-propylurea,
   1-tert-butyl-3-(7-(cyclohexylmethyl)-5,6,7,8-tetrahydroimidazo[1,5-a]pyrazin-3-yl)urea,
   7-(cyclohexylmethyl)-N-phenyl-5,6,7,8-tetrahydroimidazo[1,5-a]pyrazin-3-amine,
   7-(cyclohexylmethyl)-N-(3,5-difluorophenyl)-5,6,7,8-tetrahydroimidazo[1,5-a]pyrazin-3-amine,
   7-(cyclohexylmethyl)-N-(3-methoxyphenyl)-5,6,7,8-tetrahydroimidazo[1,5-a]pyrazin-3-amine,
   7-(cyclohexylmethyl)-N-(4-fluorophenyl)-5,6,7,8-tetrahydroimidazo[1,5-a]pyrazin-3-amine,
   7-benzyl-N-(3-chloro-2-fluorophenyl)-5,6,7,8-tetrahydroimidazo[1,5-a]pyrazin-3-amine,
   7-benzyl-N-phenyl-5,6,7,8-tetrahydroimidazo[1,5-a] pyrazin-3-amine,
   N-(3,5-difluorophenyl)-7-((tetrahydro-2H-pyran-4-yl) methyl)-5,6,7,8-tetrahydroimidazo[1,5-a]pyrazin-3-amine,
   N-phenyl-7-((tetrahydro-2H-pyran-4-yl)methyl)-5,6,7,8-tetrahydroimidazo[1,5-a]pyrazin-3-amine,
   7-benzyl-N-(2-fluorophenyl)-5,6,7,8-tetrahydroimidazo [1,5-a]pyrazin-3-amine,
   N-(4-((3-(phenylamino)-5,6-dihydroimidazo[1,5-a] pyrazin-7(8H)-yl)methyl)phenyl)acetamide,
   N-(3-methoxyphenyl)-8-((tetrahydro-2H-pyran-4-yl) methyl)-6,7,8,9-tetrahydro-5H-imidazo [1,5-a][1,4]diazepin-3-amine,
   N-(4-fluorophenyl)-8-((tetrahydro-2H-pyran-4-yl) methyl)-6,7,8,9-tetrahydro-5H-imidazo[1,5-a][1,4]diazepin-3-amine,
   N-(3-chloro-2-fluorophenyl)-8-((tetrahydro-2H-pyran-4-yl)methyl)-6,7,8,9-tetrahydro-5H-imidazo[1,5-a][1,4] diazepin-3-amine,
   N-(3,5-difluorophenyl)-8-((tetrahydro-2H-pyran-4-yl) methyl)-6,7,8,9-tetrahydro-5H-imidazo[1,5-a][1,4]diazepin-3-amine,
   3-(7-benzyl-5,6,7,8-tetrahydroimidazo[1,5-a]pyrazin-3-ylamino)phenol,
   7-(4-fluorobenzyl)-N-(5-fluoropyridin-2-yl)-5,6,7,8-tetrahydroimidazo[1,5-a]pyrazin-3-amine,
   7-benzyl-N-(4-fluorophenyl)-5,6,7,8-tetrahydroimidazo [1,5-a]pyrazin-3-amine,
   N-(2-bromo-6-chlorophenyl)-8-((tetrahydro-2H-pyran-4-yl)methyl)-6,7,8,9-tetrahydro-5H-imidazo[1,5-a][1,4] diazepin-3-amine,
   N-(7-benzyl-5,6,7,8-tetrahydroimidazo[1,5-a]pyrazin-3-yl)-N-phenylpropionamide,
   N-(7-benzyl-5,6,7,8-tetrahydroimidazo[1,5-a]pyrazin-3-yl)-N-(3-hydroxyphenyl)propionamide,
   N-(3-hydroxyphenyl)-N-(7-phenethyl-5,6,7,8-tetrahydroimidazo[1,5-a]pyrazin-3-yl)propionamide,
   7-benzyl-N-methyl-N-phenyl-5,6,7,8-tetrahydroimidazo [1,5-a]pyrazin-3-amine,
   N-benzyl-7-(cyclohexylmethyl)-5,6,7,8-tetrahydroimidazo[1,5-a]pyrazin-3-amine,
   3-benzyl-7-(cyclohexylmethyl)-5,6,7,8-tetrahydroimidazo[1,5-a]pyrazine trifluoroacetate,
   3-(4-fluorobenzyl)-7-((tetrahydro-2H-pyran-4-yl) methyl)-5,6,7,8-tetrahydroimidazo[1,5-a]pyrazine hydrochloride,
   7-(cyclohexylmethyl)-3-(4-fluorobenzyl)-5,6,7,8-tetrahydroimidazo[1,5-a]pyrazine hydrochloride,
   7-phenethyl-N-phenyl-5,6,7,8-tetrahydroimidazo[1,5-a] pyrazin-3-amine,
   N-phenyl-7-(tetrahydro-2H-pyran-4-yl)-5,6,7,8-tetrahydroimidazo[1,5-a]pyrazin-3-amine,
   N-phenyl-7-(pyridin-4-ylmethyl)-5,6,7,8-tetrahydroimidazo[1,5-a]pyrazin-3-amine,
   3-(7-phenethyl-5,6,7,8-tetrahydroimidazo[1,5-a]pyrazin-3-ylamino)phenol,
   7-(2,4-difluorobenzyl)-N-(4-fluorophenyl)-5,6,7,8-tetrahydroimidazo[1,5-a]pyrazin-3-amine,
   7-((4,4-difluorocyclohexyl)methyl)-N-(4-fluorophenyl)-5,6,7,8-tetrahydroimidazo[1,5-a]pyrazin-3-amine,
   N-(4-fluorophenyl)-7-((5-fluoropyridin-2-yl)methyl)-5,6,7,8-tetrahydroimidazo[1,5-a]pyrazin-3-amine,
   N-(4-fluorophenyl)-7-((6-fluoropyridin-3-yl)methyl)-5,6,7,8-tetrahydroimidazo[1,5-a]pyrazin-3-amine,
   N-(4-fluorophenyl)-7-((6-methoxypyridin-3-yl)methyl)-5,6,7,8-tetrahydroimidazo[1,5-a]pyrazin-3-amine,
   7-cyclohexyl-N-(4-fluorophenyl)-5,6,7,8-tetrahydroimidazo[1,5-a]pyrazin-3-amine,
   7-(3-methoxyphenethyl)-N-phenyl-5,6,7,8-tetrahydroimidazo[1,5-a]pyrazin-3-amine,
   7-(4-methoxyphenethyl)-N-phenyl-5,6,7,8-tetrahydroimidazo[1,5-a]pyrazin-3-amine,
   7-(3-(3-methoxyphenyl)propyl)-N-phenyl-5,6,7,8-tetrahydroimidazo[1,5-a]pyrazin-3-amine,
   7-(3-(4-methoxyphenyl)propyl)-N-phenyl-5,6,7,8-tetrahydroimidazo[1,5-a]pyrazin-3-amine,
   3-(2-(3-(phenylamino)-5,6-dihydroimidazo[1,5-a] pyrazin-7(8H)-yl)ethyl)phenol,
   4-(2-(3-(phenylamino)-5,6-dihydroimidazo[1,5-a] pyrazin-7(8H)-yl)ethyl)phenol,
   3-(3-(3-(phenylamino)-5,6-dihydroimidazo[1,5-a] pyrazin-7(8H)-yl)propyl)phenol, and
   4-(3-(3-(phenylamino)-5,6-dihydroimidazo[1,5-a] pyrazin-7(8H)-yl)propyl)phenol.

10. A process for the preparation of a compound of formula (I) according to claim 1, starting from a compound of formula (II):

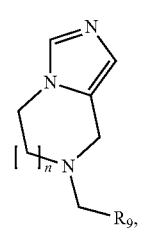

(II)

wherein n and $R_9$ are as defined in claim 1,
which compound of formula (II) is reacted with an azidating agent, in the presence of an organic base, in an inert organic solvent, at low temperatures about −78° C., to give a compound of formula (III):

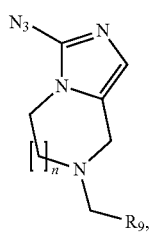

(III)

wherein n and $R_9$ are as defined in claim 1, which compound of formula (III) is subjected to a reduction by hydrogenation under a hydrogen atmosphere with a suitable catalyst in an organic solvent, including ethanol, methanol, ethyl acetate and mixtures of two of them, or alternatively, in the presence of a suitable reducing agent, including a metallic hydride, in an organic solvent, including diethyl ether, to give a compound of formula (IV):

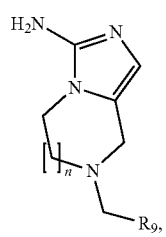

(IV)

wherein n and $R_9$ are as defined in claim 1, which compound of formula (IV) may be reacted with an isocyanate of formula $R_3$—N=C=O, wherein $R_3$ is as defined in claim 1, to give a bisurea of formula (V):

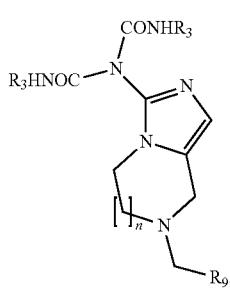

(V)

wherein n, $R_3$ and $R_9$ are as defined in claim 1, which compound of formula (V) is reacted with a base, including $K_2CO_3$, in the presence of an organic polar solvent, including MeOH, to yield a compound of formula (Ia):

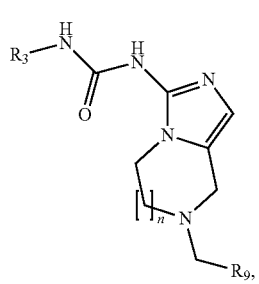

(Ia)

a particular case of the compound of formula (I), wherein $R_1$ represents a —NHCONHR$_3$ group and n, $R_3$ and $R_9$ are as defined in claim 1, or, the compound of formula (IV) as defined above may be acylated by a compound of formula $R_3$COX where X is an halogen atom and $R_3$ is as defined in claim 1, in an aprotic solvent in the presence of an organic base to yield compounds of formula (Ib):

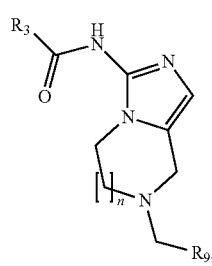

(Ib)

a particular case of the compound of formula (I), wherein $R_1$ represents a —NR$_4$COR$_3$ group, wherein $R_4$ represents a hydrogen atom, and n, $R_3$ and $R_9$ are as defined in claim 1, or, the compound of formula (IV) as defined above may be reacted with a compound of formula $R_{71}$X wherein X is an halogen atom, and $R_{71}$ is selected from the group consisting of a substituted or unsubstituted aryl group and a substituted or unsubstituted heteroaryl group, in an aprotic inert organic solvent, in the presence of a palladium catalyst and an organophosphorous ligand and a base to yield a compound of formula (Ic):

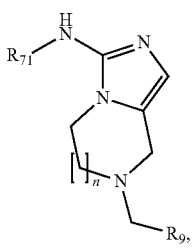

(Ic)

a particular case of the compound of formula (I), wherein $R_1$ represents —NR$_{71}$R$_{72}$, wherein $R_{71}$ is selected from the group consisting of a substituted or unsubstituted aryl group and a substituted or unsubstituted heteroaryl group, $R_{72}$ represents a hydrogen atom, and n and $R_9$ are as defined in claim 1, which compound of formula (Ic) may be subjected to an acylation reaction with a compound of formula R₃COX, wherein X is an halogen atom and R₃ is as defined in claim 1, in an aprotic solvent in the presence of an organic base to yield a compound of formula (Id):

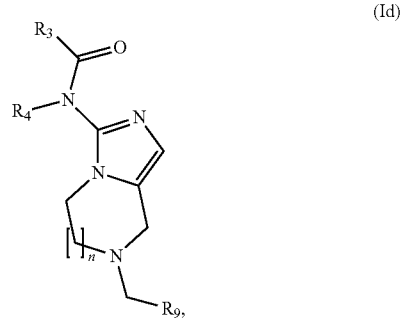

a particular case of the compound of formula (I), wherein $R_1$ represents a —NR₄COR₃ group, wherein n, $R_3$ and $R_9$ are as defined in claim 1, and $R_4$ is selected from the group consisting of a substituted or unsubstituted aryl group and a substituted or unsubstituted heteroaryl group, or the compound of formula (Ic) may be reacted with a compound of formula R₇₂X, wherein X is an halogen atom, and $R_{72}$ is a linear or branched, substituted or unsubstituted $C_{1-3}$alkyl group, a linear or branched, substituted or unsubstituted $C_{2-3}$alkenyl group, or a linear or branched, substituted or unsubstituted $C_{2-3}$alkynyl group, in an aprotic polar organic solvent in the presence of a base to yield a compound of formula (Ie):

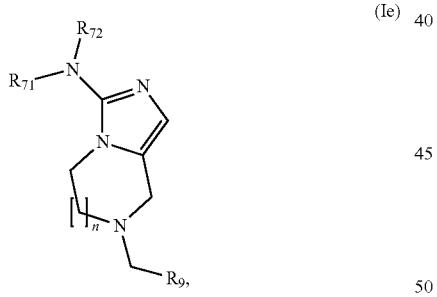

a particular case of the compound of formula (I), wherein $R_1$ represents a —NR₇₁R₇₂ group, wherein $R_{71}$ is selected from the group consisting of a substituted or unsubstituted aryl group and a substituted or unsubstituted heteroaryl group, $R_{72}$ represents a linear or branched, substituted or unsubstituted $C_{1-3}$alkyl group, a linear or branched, substituted or unsubstituted $C_{2-3}$alkenyl group, a linear or branched, substituted or unsubstituted $C_{2-3}$alkynyl group, and n and $R_9$ are as defined in claim 1, or the compound of formula (Ic), in the case where $R_9$ represents a phenyl group, may be debenzylated following hydrogenation under palladium catalysis in the presence of an organic solvent to give a compound of formula (VI):

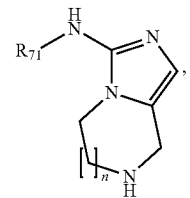

wherein $R_{71}$ is selected from the group consisting of a substituted or unsubstituted aryl group and a substituted or unsubstituted heteroaryl group, and n is as defined in claim 1, which compound of formula (VI) is then subjected to a reductive amination process by reaction with aldehydes or ketones of formula $R_2$=O, where $R_2$ is as defined in claim 1, in the presence of a reducing agent in an inert organic solvent to yield a compound of formula (If):

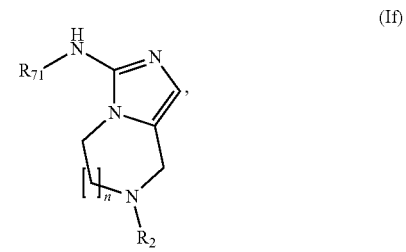

a particular case of the compound of formula (I), wherein $R_1$ represents a —NR₇₁R₇₂ group, wherein $R_{71}$ is selected from the group consisting of a substituted or unsubstituted aryl group and a substituted or unsubstituted heteroaryl group, $R_{72}$ represents a hydrogen atom, and, n and $R_2$ are as defined in claim 1.

11. A process for the preparation of a compound of formula (I) according to claim 1 starting from a compound of formula (IV)

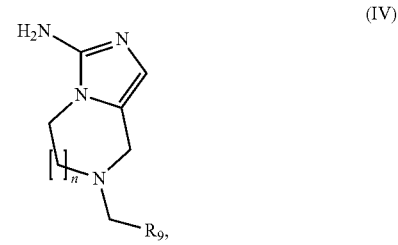

wherein n and $R_9$ are as defined in claim 1,
which compound of formula (IV) is subjected to a reductive amination process by reaction with an aldehyde or ketone of formula $R_{71}$=O, wherein $R_{71}$ represents a linear or branched, substituted or unsubstituted $C_{1-10}$ $C_{1-10}$alkyl group, a linear or branched, substituted or unsubstituted $C_{2-10}$alkenyl group, a linear or branched, substituted or unsubstituted $C_{2-10}$alkynyl group, a substituted or unsubstituted cycloalkyl group, a substituted or unsubstituted cycloalkylalkyl group, a substituted or unsubstituted arylalkyl group, a substituted or unsubstituted heterocycloalkyl group, a substituted or unsubstituted heterocycloalkylalkyl group, or an unsubstituted heteroarylalkyl group, in the presence of a reducing agent in an inert organic solvent to yield a compound of formula (Ig):

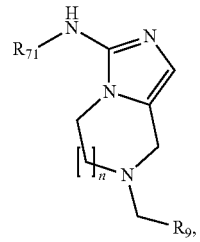

(Ig)

a particular case of the compound of formula (I), wherein $R_1$ represents a $-NR_{71}R_{72}$ group, wherein $R_{71}$ is selected from the group consisting of a linear or branched, substituted or unsubstituted $C_{1-10}$alkyl group, a linear or branched, substituted or unsubstituted $C_{2-10}$alkenyl group, a linear or branched, substituted or unsubstituted $C_{2-10}$alkynyl group, a substituted or unsubstituted cycloalkyl group, a a substituted or unsubstituted cycloalkylalkyl group, a substituted or unsubstituted arylalkyl group, a substituted or unsubstituted heterocycloalkyl group, a substituted or unsubstituted heterocycloalkylalkyl group, or an unsubstituted heteroarylalkyl group, $R_{72}$ represents a hydrogen atom, and n and $R_9$ are as defined in claim 1.

12. A process for the preparation of a compound of formula (I) according to claim 1, starting from a compound of formula (II):

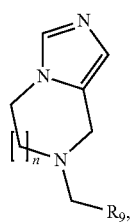

(II)

wherein n and $R_9$ are as defined in claim 1, which compound of formula (II) is reacted with a compound of formula $R_6-(C(R_{51}R_{52}))_{(m')}-CHO$, wherein $R_6$, $R_{51}$, $R_{52}$ are as defined in claim 1, and m' is 0, 1 or 2, to give a compound of formula (VII):

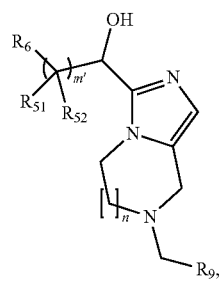

(VII)

wherein $R_{51}$, $R_{52}$, $R_6$, m' and n are as defined above and $R_9$ is as defined in claim 1, which compound of formula (VII) is reduced in the presence of an organosilane, and an acid to yield a compound of formula (Ih):

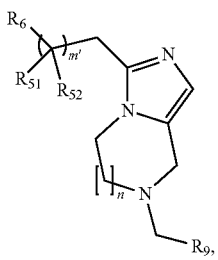

(Ih)

a particular case of the compound of formula (I), wherein $R_1$ represents $R_6-(C(R_{51}R_{52}))m'-CH_2-$, and $R_{51}$, $R_{52}$, $R_6$, $R_9$, m' and n are as defined above.

13. A method for the treatment of a sigma receptor mediated disease or condition selected from the group consisting of diarrhea, lipoprotein disorders, hyperlipidemia, hypertriglyceridemia, hypercholesterolemia, obesity, migraine, pain, arthritis, hypertension, arrhythmia, ulcer, glaucoma, learning deficits, memory deficits, attention deficits, cognition disorders, demyelinating diseases, addiction to drugs and chemical substances including cocaine, amphetamine, ethanol and nicotine; tardive dyskinesia, epilepsy, stroke, stress, psychotic conditions, depression, anxiety, and schizophrenia in a subject in need thereof, comprising administration of an effective amount of the compound according to claim 1.

14. A method for the treatment of neuropathic pain, inflammatory pain or other pain conditions involving allodynia and/or hyperalgesia in a subject in need thereof, comprising administration of an effective amount of the compound according to claim 1.

15. A pharmaceutical composition comprising the compound according to claim 1, or a pharmaceutically acceptable salt, isomer, or solvate thereof, and at least a pharmaceutically acceptable carrier, additive, adjuvant or vehicle.

* * * * *

UNITED STATES PATENT AND TRADEMARK OFFICE
CERTIFICATE OF CORRECTION

PATENT NO. : 9,676,784 B2
APPLICATION NO. : 15/105105
DATED : June 13, 2017
INVENTOR(S) : José-Luis Díaz-Fernández, Carmen Almansa-Rosales and Piotr Nieczypor Page 1 of 1

It is certified that error appears in the above-identified patent and that said Letters Patent is hereby corrected as shown below:

In the Claims

Column 60, Line 60: "$C_{1-10}$ $C_{1-10}$ alkyl" should be --$C_{1-10}$ alkyl--.

Signed and Sealed this
Third Day of April, 2018

Andrei Iancu
*Director of the United States Patent and Trademark Office*